United States Patent [19]
Funder et al.

[11] Patent Number: 5,883,240
[45] Date of Patent: Mar. 16, 1999

[54] GENETIC SEQUENCES ENCODING GLUCOCORTICOID DEHYDROGENASES AND USES THEREFOR

[75] Inventors: John W. Funder, North Carlton; Anthony L. Albiston, North Balwyn; Varuni R. Obeyesekere, Malvern; Zygmunt S. Krozowski, Wheelers Hill; Robin E. Smith, Murrumbeena, all of Australia

[73] Assignee: Baker Medical Research Institute, Victoria, Australia

[21] Appl. No.: 519,081

[22] Filed: Aug. 24, 1995

[51] Int. Cl.$^6$ ................................................ C12N 15/53
[52] U.S. Cl. .......................................... 536/23.2; 435/190
[58] Field of Search .................................. 435/69.1, 70.1, 435/71.1, 72.1, 190, 252.3, 320.1; 536/23.2

[56] References Cited

FOREIGN PATENT DOCUMENTS 9421815  9/1994  WIPO .

OTHER PUBLICATIONS

Michael, A.E. et al., *The Lancet*, 342: 711–12 (1993) (Exhibit 2).
Agarwal, A.K. et al., *J. Bio. Chem.*, 269: 25959–62 (1994) (Exhibit 3).
Albiston et al. (Nov. 1994) Mol. Cell. Endocrin. 105: R11–R17. "Cloning and tissue distribution of the human 11β–hydroxysteroid dehydrogenas type z enzyme" .
Hillier et al. (Feb. 1995), Wash–U–Merck EST project, accession T52701, T52702.
Wv et al. (1993) J. Biol Chem 2 68:12964–12969 "Expression cloning and characterization of human 17β–hydroxysteriod dehydrogenase ...".

*Primary Examiner*—Charles L. Patterson, Jr.
*Attorney, Agent, or Firm*—John P. White; Cooper & Dunham LLP

[57] ABSTRACT

The present invention relates generally to a nucleic acid molecule encoding, or complementary to a nucleic acid molecule encoding, a recombinant NAD+ dependent glucocorticoid dehydrogenase and more particularly to 11 β-hydroxysteroid dehydrogenase-2 (11 βHSD2). When expressed in a prokaryotic or eukaryotic cell, the nucleic acid molecule of the present invention is used to assay for potential agonists or antagonist of glucocorticoid dehydrogenase activity. Further, the present invention relates to inmmunoreactive molecules to NAD+ dependent glucocorticold dehydrogenase which provide the basis for a new range of diagnostic agents for use, such as in the diagnosis and treatment of hypertension and in predicting the potential outcome of in vitro fertilization and embryo transfer procedures.

8 Claims, 8 Drawing Sheets

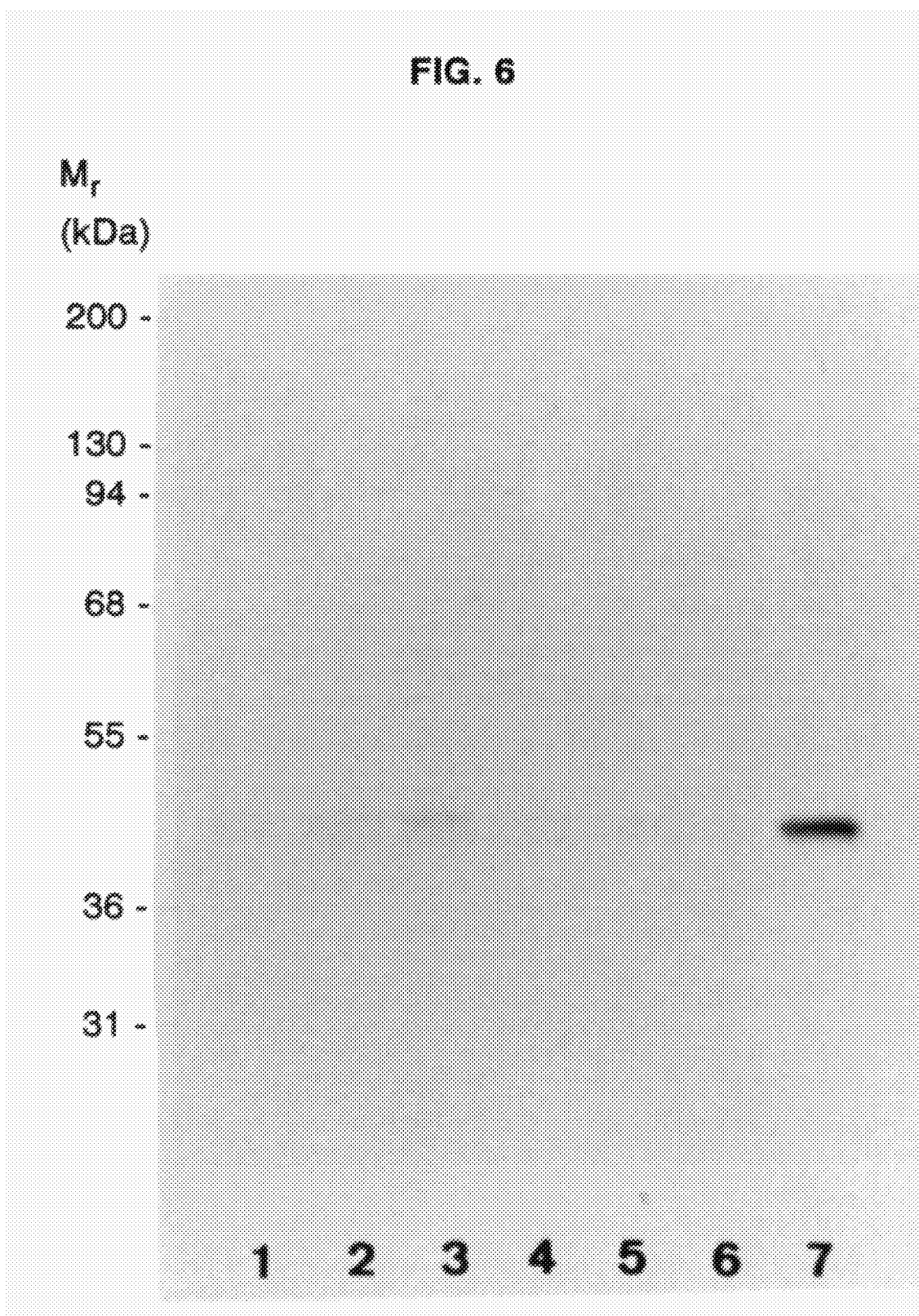

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1881 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE:

( v i ) ORIGINAL SOURCE:
        ( A ) ORGANISM: Homo sapiens
        ( F ) TISSUE TYPE: Kidney ( v i i ) IMMEDIATE SOURCE:
        ( B ) CLONE: 11BHSD2

( i x ) FEATURE:
        ( A ) NAME/KEY: CDS
        ( B ) LOCATION: 109..1323

( x i ) SEQUENCE DESCRIPTION: SEQ ID NO:1:

```
CGCGCCCCAG   GCCGGTGTAC   CCCCGCACTC   CGCGCCCCGG   CCTAGAAGCT   CTCTCTCCCC        60

GCTCCCCGGC   CCGGCCCCCG   CCCCGCCCCG   CCCCAGCCCG   CTGGCGCC  ATG  GAG  CGC       117
                                                            Met  Glu  Arg
                                                             1

TGG  CCT  TGG  CCG  TCG  GGC  GGC  GCC  TGG  CTG  CTC  GTG  GCT  GCC  CGC  GCG   165
Trp  Pro  Trp  Pro  Ser  Gly  Gly  Ala  Trp  Leu  Leu  Val  Ala  Ala  Arg  Ala
      5                   10                        15

CTG  CTG  CAG  CTG  CTG  CGC  TCA  GAC  CTG  CGT  CTG  GGC  CGC  CCG  CTG  CTG   213
Leu  Leu  Gln  Leu  Leu  Arg  Ser  Asp  Leu  Arg  Leu  Gly  Arg  Pro  Leu  Leu
```

|  20 | | | | 25 | | | | 30 | | | | 35 | | | | |
|---|---|---|---|---|---|---|---|---|---|---|---|---|---|---|---|---|
| GCG | GCG | CTG | GCG | CTG | CTG | GCC | GCG | CTC | GAC | TGG | CTG | TGC | CAG | CGC | CTG | 261 |
| Ala | Ala | Leu | Ala | Leu | Leu | Ala | Ala | Leu | Asp | Trp | Leu | Cys | Gln | Arg | Leu | |
| | | | | 40 | | | | | 45 | | | | | 50 | | |
| CTG | CCC | CCG | CCG | GCC | GCA | CTC | GCC | GTG | CTG | GCC | GCC | GCC | GGC | TGG | ATC | 309 |
| Leu | Pro | Pro | Pro | Ala | Ala | Leu | Ala | Val | Leu | Ala | Ala | Ala | Gly | Trp | Ile | |
| | | | 55 | | | | | 60 | | | | | 65 | | | |
| GCG | TTG | TCC | CGC | CTG | GCG | CGC | CCG | CAG | CGC | CTG | CCG | GTG | GCC | ACT | CGC | 357 |
| Ala | Leu | Ser | Arg | Leu | Ala | Arg | Pro | Gln | Arg | Leu | Pro | Val | Ala | Thr | Arg | |
| | | 70 | | | | | 75 | | | | | 80 | | | | |
| GCG | GTG | CTC | ATC | ACC | GGC | TGT | GAC | TCT | GGT | TTT | GGC | AAG | GAG | ACG | GCC | 405 |
| Ala | Val | Leu | Ile | Thr | Gly | Cys | Asp | Ser | Gly | Phe | Gly | Lys | Glu | Thr | Ala | |
| | 85 | | | | | 90 | | | | | 95 | | | | | |
| AAG | AAA | CTG | GAC | TCC | ATG | GGC | TTC | ACG | GTG | CTG | GCC | ACC | GTA | TTG | GAG | 453 |
| Lys | Lys | Leu | Asp | Ser | Met | Gly | Phe | Thr | Val | Leu | Ala | Thr | Val | Leu | Glu | |
| 100 | | | | | 105 | | | | | 110 | | | | | 115 | |
| TTG | AAC | AGC | CCC | GGT | GCC | ATC | GAG | CTG | CGT | ACC | TGC | TGC | TCC | CCT | CGC | 501 |
| Leu | Asn | Ser | Pro | Gly | Ala | Ile | Glu | Leu | Arg | Thr | Cys | Cys | Ser | Pro | Arg | |
| | | | | 120 | | | | | 125 | | | | | 130 | | |
| CTA | AGG | CTG | CTG | CAG | ATG | GAC | CTG | ACC | AAA | CCA | GGA | GAC | ATT | AGC | CGC | 549 |
| Leu | Arg | Leu | Leu | Gln | Met | Asp | Leu | Thr | Lys | Pro | Gly | Asp | Ile | Ser | Arg | |
| | | | 135 | | | | | 140 | | | | | 145 | | | |
| TTG | CTA | GAG | TTC | ACC | AAG | GCC | CAC | ACC | ACC | AGC | ACC | GGC | CTG | TGG | GGC | 597 |
| Leu | Leu | Glu | Phe | Thr | Lys | Ala | His | Thr | Thr | Ser | Thr | Gly | Leu | Trp | Gly | |
| | | 150 | | | | | 155 | | | | | 160 | | | | |
| CTC | GTC | AAC | AAC | GCA | GGC | CAC | AAT | GAA | GTA | GTT | GCT | GAT | GCG | GAG | CTG | 645 |
| Leu | Val | Asn | Asn | Ala | Gly | His | Asn | Glu | Val | Val | Ala | Asp | Ala | Glu | Leu | |
| | 165 | | | | | 170 | | | | | 175 | | | | | |
| TCT | CCA | GTG | GCC | ACT | TTC | CGT | AGC | TGC | ATG | GAG | GTG | AAT | TTC | TTT | GGC | 693 |
| Ser | Pro | Val | Ala | Thr | Phe | Arg | Ser | Cys | Met | Glu | Val | Asn | Phe | Phe | Gly | |
| 180 | | | | | 185 | | | | | 190 | | | | | 195 | |
| GCG | CTC | GAG | CTG | ACC | AAG | GGC | CTC | CTG | CCC | CTG | CTG | CGC | AGC | TCA | AGG | 741 |
| Ala | Leu | Glu | Leu | Thr | Lys | Gly | Leu | Leu | Pro | Leu | Leu | Arg | Ser | Ser | Arg | |
| | | | | 200 | | | | | 205 | | | | | 210 | | |
| GGC | CGC | ATC | GTG | ACT | GTG | GGG | AGC | CCA | GCG | GGG | GAC | ATG | CCA | TAT | CCG | 789 |
| Gly | Arg | Ile | Val | Thr | Val | Gly | Ser | Pro | Ala | Gly | Asp | Met | Pro | Tyr | Pro | |
| | | | 215 | | | | | 220 | | | | | 225 | | | |
| TGC | TTG | GGG | GCC | TAT | GGA | ACC | TCC | AAA | GCG | GCC | GTG | GCG | CTA | CTC | ATG | 837 |
| Cys | Leu | Gly | Ala | Tyr | Gly | Thr | Ser | Lys | Ala | Ala | Val | Ala | Leu | Leu | Met | |
| | | 230 | | | | | 235 | | | | | 240 | | | | |
| GAC | ACA | TTC | AGC | TGT | GAA | CTC | CTT | CCC | TGG | GGG | GTC | AAG | GTC | AGC | ATC | 885 |
| Asp | Thr | Phe | Ser | Cys | Glu | Leu | Leu | Pro | Trp | Gly | Val | Lys | Val | Ser | Ile | |
| | 245 | | | | | 250 | | | | | 255 | | | | | |
| ATC | CAG | CCT | GGC | TGC | TTC | AAG | ACA | GAG | TCA | GTG | AGA | AAC | GTG | GGT | CAG | 933 |
| Ile | Gln | Pro | Gly | Cys | Phe | Lys | Thr | Glu | Ser | Val | Arg | Asn | Val | Gly | Gln | |
| 260 | | | | | 265 | | | | | 270 | | | | | 275 | |
| TGG | GAA | AAG | CGC | AAG | CAA | TTG | CTG | CTG | GCC | AAC | CTG | CCT | CAA | GAG | CTG | 981 |
| Trp | Glu | Lys | Arg | Lys | Gln | Leu | Leu | Leu | Ala | Asn | Leu | Pro | Gln | Glu | Leu | |
| | | | | 280 | | | | | 285 | | | | | 290 | | |
| CTG | CAG | GCC | TAC | GGC | AAG | GAC | TAC | ATC | GAG | CAC | TTG | CAT | GGG | CAG | TTC | 1029 |
| Leu | Gln | Ala | Tyr | Gly | Lys | Asp | Tyr | Ile | Glu | His | Leu | His | Gly | Gln | Phe | |
| | | | 295 | | | | | 300 | | | | | 305 | | | |
| CTG | CAC | TCG | CTA | CGC | CTG | GCC | ATG | TCC | GAC | CTC | ACC | CCA | GTT | GTA | GAT | 1077 |
| Leu | His | Ser | Leu | Arg | Leu | Ala | Met | Ser | Asp | Leu | Thr | Pro | Val | Val | Asp | |
| | | 310 | | | | | 315 | | | | | 320 | | | | |
| GCC | ATC | ACA | GAT | GCG | CTG | CTG | GCA | GCT | CGG | CCC | CGC | CGC | CGC | TAT | TAC | 1125 |
| Ala | Ile | Thr | Asp | Ala | Leu | Leu | Ala | Ala | Arg | Pro | Arg | Arg | Arg | Tyr | Tyr | |
| | 325 | | | | | 330 | | | | | 335 | | | | | |
| CCC | GGC | CAG | GGC | CTG | GGG | CTC | ATG | TAC | TTC | ATC | CAC | TAC | TAC | CTG | CCT | 1173 |
| Pro | Gly | Gln | Gly | Leu | Gly | Leu | Met | Tyr | Phe | Ile | His | Tyr | Tyr | Leu | Pro | |

|   |   |   |   |   |   |   |   |   |   |   |   |   |   |   |   |   |
|---|---|---|---|---|---|---|---|---|---|---|---|---|---|---|---|---|
| 340 | | | | | 345 | | | | | 350 | | | | | 355 | |
| GAA | GGC | CTG | CGG | CGC | CGC | TTC | CTG | CAG | GCC | TTC | TTC | ATC | AGT | CAC | TGT | 1221 |
| Glu | Gly | Leu | Arg | Arg | Arg | Phe | Leu | Gln | Ala | Phe | Phe | Ile | Ser | His | Cys | |
| | | | 360 | | | | | 365 | | | | | | 370 | | |
| CTG | CCT | CGA | GCA | CTG | CAG | CCT | GGC | CAG | CCT | GGC | ACT | ACC | CCA | CCA | CAG | 1269 |
| Leu | Pro | Arg | Ala | Leu | Gln | Pro | Gly | Gln | Pro | Gly | Thr | Thr | Pro | Pro | Gln | |
| | | | 375 | | | | | 380 | | | | | | 385 | | |
| GAC | GCA | GCC | CAG | GAC | CCA | AAC | CTG | AGC | CCC | GGC | CCT | TCC | CCA | GCA | GTG | 1317 |
| Asp | Ala | Ala | Gln | Asp | Pro | Asn | Leu | Ser | Pro | Gly | Pro | Ser | Pro | Ala | Val | |
| | | | 390 | | | | | 395 | | | | | | 400 | | |
| GCT | CGG | TGAGCCATGT | | GCACCTATGG | | CCCAGCCACT | | GCAGCACAGG | | AGGCTCCGTG | | | | | | 1373 |
| Ala | Arg | | | | | | | | | | | | | | | |
| | 405 | | | | | | | | | | | | | | | |

```
AGCCTTGGTT  CCTCCCCGAA  AACCCCCAGC  ATTACGATCC  CCCAAGTGTC  CTGGACCCTG       1433

GCCTAAAGAA  TCCCACCCCC  ACTTCATGCC  CACTGCCGAT  GCCCAATCCA  GGCCCGGTGA       1493

GGCCAAGGTT  TCCCAGTGAG  CCTCTGCGCC  TCTCCACTGT  TCATGAGCC   CAAACACCCT       1553

CCTGGCACAA  CGCTCTACCC  TGCAGCTTGG  AGAACTCCGC  TGGATGGGAG  TCTCATGCAA       1613

GACTTCACTG  CAGCCTTTCA  CAGGACTCTG  CAGATAGTGC  CTCTGCAAAC  TAAGGAGTGA       1673

CTAGGTGGGT  TGGGGACCCC  CTCAGGATTG  TTTCTCGGCA  CCAGTGCCTC  AGTGCTGCAA       1733

TTGAGGGCTA  AATCCCAAGT  GTCTCTTGAC  TGGCTCAAGA  ATTAGGGCCC  CAACTACACA       1793

CCCCCAAGCC  ACAGGGAAGC  ATGTACTGTA  CTTCCCAATT  GCCACATTTT  AAATAAAGAC       1853

AAATTTTTAT  TTCTTCTAAA  AAAAAAA                                             1881
```

(2) INFORMATION FOR SEQ ID NO:2:

(i) SEQUENCE CHARACTERISTICS:
        (A) LENGTH: 405 amino acids
        (B) TYPE: amino acid
        (D) TOPOLOGY: linear (ii) MOLECULE TYPE: protein (xi) SEQUENCE DESCRIPTION: SEQ ID NO:2:

| Met | Glu | Arg | Trp | Pro | Trp | Pro | Ser | Gly | Gly | Ala | Trp | Leu | Leu | Val | Ala |
|---|---|---|---|---|---|---|---|---|---|---|---|---|---|---|---|
| 1 | | | | 5 | | | | | 10 | | | | | 15 | |

| Ala | Arg | Ala | Leu | Leu | Gln | Leu | Leu | Arg | Ser | Asp | Leu | Arg | Leu | Gly | Arg |
|---|---|---|---|---|---|---|---|---|---|---|---|---|---|---|---|
| | | | 20 | | | | | 25 | | | | | 30 | | |

| Pro | Leu | Leu | Ala | Ala | Leu | Ala | Leu | Leu | Ala | Ala | Leu | Asp | Trp | Leu | Cys |
|---|---|---|---|---|---|---|---|---|---|---|---|---|---|---|---|
| | | | 35 | | | | | 40 | | | | | 45 | | |

| Gln | Arg | Leu | Leu | Pro | Pro | Pro | Ala | Ala | Leu | Ala | Val | Leu | Ala | Ala | Ala |
|---|---|---|---|---|---|---|---|---|---|---|---|---|---|---|---|
| | 50 | | | | | 55 | | | | | 60 | | | | |

| Gly | Trp | Ile | Ala | Leu | Ser | Arg | Leu | Ala | Arg | Pro | Gln | Arg | Leu | Pro | Val |
|---|---|---|---|---|---|---|---|---|---|---|---|---|---|---|---|
| 65 | | | | | 70 | | | | | 75 | | | | | 80 |

| Ala | Thr | Arg | Ala | Val | Leu | Ile | Thr | Gly | Cys | Asp | Ser | Gly | Phe | Gly | Lys |
|---|---|---|---|---|---|---|---|---|---|---|---|---|---|---|---|
| | | | | 85 | | | | | 90 | | | | | 95 | |

| Glu | Thr | Ala | Lys | Lys | Leu | Asp | Ser | Met | Gly | Phe | Thr | Val | Leu | Ala | Thr |
|---|---|---|---|---|---|---|---|---|---|---|---|---|---|---|---|
| | | | 100 | | | | | 105 | | | | | 110 | | |

| Val | Leu | Glu | Leu | Asn | Ser | Pro | Gly | Ala | Ile | Glu | Leu | Arg | Thr | Cys | Cys |
|---|---|---|---|---|---|---|---|---|---|---|---|---|---|---|---|
| | | | 115 | | | | | 120 | | | | | 125 | | |

| Ser | Pro | Arg | Leu | Arg | Leu | Leu | Gln | Met | Asp | Leu | Thr | Lys | Pro | Gly | Asp |
|---|---|---|---|---|---|---|---|---|---|---|---|---|---|---|---|
| | | | 130 | | | | | 135 | | | | | 140 | | |

| Ile | Ser | Arg | Leu | Leu | Glu | Phe | Thr | Lys | Ala | His | Thr | Thr | Ser | Thr | Gly |
|---|---|---|---|---|---|---|---|---|---|---|---|---|---|---|---|
| 145 | | | | | 150 | | | | | 155 | | | | | 160 |

| Leu | Trp | Gly | Leu | Val | Asn | Asn | Ala | Gly | His | Asn | Glu | Val | Val | Ala | Asp |
|---|---|---|---|---|---|---|---|---|---|---|---|---|---|---|---|
| | | | | 165 | | | | | 170 | | | | | 175 | |

```
Ala  Glu  Leu  Ser  Pro  Val  Ala  Thr  Phe  Arg  Ser  Cys  Met  Glu  Val  Asn
              180                      185                      190

Phe  Phe  Gly  Ala  Leu  Glu  Leu  Thr  Lys  Gly  Leu  Leu  Pro  Leu  Leu  Arg
         195                      200                      205

Ser  Ser  Arg  Gly  Arg  Ile  Val  Thr  Val  Gly  Ser  Pro  Ala  Gly  Asp  Met
     210                      215                      220

Pro  Tyr  Pro  Cys  Leu  Gly  Ala  Tyr  Gly  Thr  Ser  Lys  Ala  Ala  Val  Ala
225                           230                 235                           240

Leu  Leu  Met  Asp  Thr  Phe  Ser  Cys  Glu  Leu  Leu  Pro  Trp  Gly  Val  Lys
                    245                      250                           255

Val  Ser  Ile  Ile  Gln  Pro  Gly  Cys  Phe  Lys  Thr  Glu  Ser  Val  Arg  Asn
               260                      265                      270

Val  Gly  Gln  Trp  Glu  Lys  Arg  Lys  Gln  Leu  Leu  Leu  Ala  Asn  Leu  Pro
          275                      280                      285

Gln  Glu  Leu  Leu  Gln  Ala  Tyr  Gly  Lys  Asp  Tyr  Ile  Glu  His  Leu  His
     290                      295                 300

Gly  Gln  Phe  Leu  His  Ser  Leu  Arg  Leu  Ala  Met  Ser  Asp  Leu  Thr  Pro
305                      310                 315                           320

Val  Val  Asp  Ala  Ile  Thr  Asp  Ala  Leu  Leu  Ala  Ala  Arg  Pro  Arg  Arg
               325                      330                      335

Arg  Tyr  Tyr  Pro  Gly  Gln  Gly  Leu  Gly  Leu  Met  Tyr  Phe  Ile  His  Tyr
               340                      345                      350

Tyr  Leu  Pro  Glu  Gly  Leu  Arg  Arg  Arg  Phe  Leu  Gln  Ala  Phe  Phe  Ile
          355                      360                      365

Ser  His  Cys  Leu  Pro  Arg  Ala  Leu  Gln  Pro  Gly  Gln  Pro  Gly  Thr  Thr
     370                      375                 380

Pro  Pro  Gln  Asp  Ala  Ala  Gln  Asp  Pro  Asn  Leu  Ser  Pro  Gly  Pro  Ser
385                      390                      395                           400

Pro  Ala  Val  Ala  Arg
                    405
```

( 2 ) INFORMATION FOR SEQ ID NO:3:

( i ) SEQUENCE CHARACTERISTICS:
( A ) LENGTH: 16 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: C-terminal ( v i ) ORIGINAL SOURCE:
( A ) ORGANISM: Homo sapiens
( F ) TISSUE TYPE: Kidney ( v i i ) IMMEDIATE SOURCE:
( B ) CLONE: HUHPEP3

( i x ) FEATURE:
( A ) NAME/KEY: Peptide
( B ) LOCATION: 1..16

( x i ) SEQUENCE DESCRIPTION: SEQ ID NO:3:

```
Cys  Gln  Asp  Pro  Asn  Leu  Ser  Pro  Gly  Pro  Ser  Pro  Ala  Val  Ala  Arg
1                   5                      10                           15
```

GENETIC SEQUENCES ENCODING GLUCOCORTICOID DEHYDROGENASES AND USES THEREFOR

FIELD OF THE INVENTION

The present invention relates generally to a nucleic acid molecule encoding, or complementary to a molecule encoding, a recombinant 11 β-dehydrogenase of the glucocorticoid metabolic pathway, and more particularly to a molecule having 11 β-hydroxysteroid dehydrogenase-2 (11 βHSD2) activity, and/or enzymatically active and/or immunologically interactive parts thereof. The nucleic acid molecule and immuno-interactive molecules of the present invention exhibit a range of beneficial properties, including the development of diagnostics for the treatment of hypertension and to determine the potential outcome of an in vitro fertilisation (IVF) regime. Furthermore, the present invention provides therapeutic and/or diagnostic reagents comprising said immunologically interactive molecules.

Bibliographic details of the publications referred to by author in this specification are collected at the end of the description. Sequence identity numbers (SEQ ID NOs.) for the nucleotide and amino acid sequences referred to in the specification are defined after the bibliography.

Throughout the specification, unless the context requires otherwise, the word "comprises", or variations such as "comprises" or "comprising" will be understood to imply the inclusion of a stated element or integer or group of elements or integers but not the exclusion of any other element or integer or group of elements or integers.

BACKGROUND TO THE INVENTION

Improvements in recombinant DNA technology have produced dramatic changes to the nature of pharmaceutical and agricultural industries. One area where this technology has had great impact is in the development of diagnostics, in particular diagnostics to determine the suitability of candidates for IVF regimens. Traditionally, there has been no efficient means of predicting the outcome of an IVF programme, which is a costly procedure. Furthermore, recombinant DNA technology has led to advances in the development of diagnostics for assessing the hypertensive state of patients.

Corticosteroids, also referred to as glucocorticoids are steroid hormones, the most common form of which is cortisol. Modulation of glucocorticoid activity is important in regulating physiological processes in a wide range of tissues and organs. Glucocorticoids act within the gonads to directly suppress testosterone production (Monder et al., 1994). High levels of glucocorticoids may also result in excessive salt and water retention by the kidneys, producing high blood pressure.

Glucocorticoid action is mediated via binding of the molecule to a receptor, defined hereinafter as either a mineralocorticoid receptor (MR) or a glucocorticoid receptor (GR). Krozowski et al.(1983) and Beaumont and Fanestil (1983) showed that MR of adrenalectomised rats have an equal affinity for the mineralocorticoid aldosterone and glucocorticoids, for example corticosterone and cortisol. Confirmatory evidence has been found for human MR (Arriza et al., 1988). In patients suffering from the congenital syndrome of Apparent Mineralocorticoid Excess (AME; Ulick et al., 1979), cortisol levels are elevated and bind to and activate MRs normally occupied by aldosterone, the steroid that regulates salt and water balance in the body. Salt and water are retained in AME patients causing severe hypertension.

The enzyme 11 β-hydroxysteroid dehydrogenase (11 βHSD) converts glucocorticoids into metabolites that are unable to bind to MRs (Edwards et al., 1988; Funder et al., 1988), present in mineralocorticoid target tissues, for example kidney, pancreas, small intestine, colon, as well as the hippocampus, placenta and gonads. For example, in aldosterone target tissues 11 βHSD inactivates glucocorticoid molecules, allowing the much lower circulating levels of aldosterone to maintain renal homeostasis. When the 11 βHSD enzyme is inactivated, for example in AME patients (Ulick et al., 1979) or following administration of glycyrrhetinic acid, a component of licorice, severe hypertension results. Further, placental 11 βHSD activity may protect the foetus from high circulating levels of glucocorticoid which may predispose to hypertension in later life (Edwards et al., 1993).

Although the 11 βHSD enzyme has never been purified to homogeneity, biochemical characterisation of 11 βHSD activity indicates the presence of at least two isoenzymes (11 βHSD1 and 11 βHSD2) with different cofactor requirements and substrate affinities. The 11 βHSD1 enzyme is a low affinity enzyme that prefers NADP+ as a cofactor (Agarwal et al., 1989). The 11 βHSD2 enzyme is a high affinity enzyme (Km for glucocorticoid=10 nM), requiring NAD+, not NADP+ as the preferred cofactor, belonging to a class of glucocorticoid dehydrogenase enzymes hereinafter referred to as"NAD+ dependent glucocorticoid dehydrogenase" enzymes. p Michael et al. (1993) show an inverse correlation between 11 βHSD enzyme activity in human granulosa-lutein cells and the success of IVF, and suggest that activity of this enzyme might be related to the success of embryo attachment and implantation following IVF. The measurement of ovarian 11 βHSD enzyme activity as a prognostic indicator for the outcome of assisted conception in all species, is the subject of UK Patent Application No 9305984. However, the disclosure of Michael et al. (1993), and corresponding UK Patent Application No 9305984 do not identify, or even suggest which isoenzyme in the ovary might be a predictive indicator of IVF embryo transfer, or a means of distinguishing isoenzymes of 11 βHSD in the prediction of IVF embryo transfer outcomes. In fact, the enzyme assay procedure might detect all isoenzymes of 11 βHSD activity in the cell, some of which may be hitherto uncharacterised.

Clearly, there are direct benefits to be derived from interventionary measures that modulate glucocorticoid levels in humans, for example using gene therapies. The gene encoding the NADP+ dependent glucocorticoid dehydrogenase enzyme 11 βHSD1, has been cloned from rat cells (Agarwal et al., 1989). Analysis of the 11 βHSD1 gene from AME patients (Nikknia et al., 1993) has failed to identify a potential correlation between activity of this particular genetic sequence and the syndrome. Furthermore, the isolation of the human 11 βHSD1 gene has not contributed to the identification of other genes that do in fact play a role in the aetiology of diseases associated with glucocorticoid metabolism, for example AME. In particular, the molecular characterisation of a gene encoding the 11 βHSD2 enzyme from human kidney cells, has not been a straightforward procedure. For example, the enzyme has not been purified to homogeneity and, until the present invention, there were no nucleotide sequence or amino acid sequence data for the 11 βHSD2 enzyme from any primate species, including man.

SUMMARY OF THE INVENTION

In accordance with the present invention, genetic sequences encoding a human NAD+ dependent dehydrogenase enzyme that metabolises glucocorticoids, preferably cortisol, to the 11-dehydro metabolite, have been cloned, enabling for the first time, the development of gene therapies which alter the endogenous activity of the NAD+ dependent glucocorticoid dehydrogenase enzyme in a cell. The present invention also permits the screening, through genetic or immunological means, levels of expression of genes encoding the NAD+ dependent glucocorticoid dehydrogenase enzyme in various tissue or organ types, including for example, skin, colon, kidney, placenta, and gonads, amongst others.

Further, the present invention permits said screening as a diagnostic for hypertension, in the syndrome of AME, or in predicting the success of an in vitro fertilisation regime.

Accordingly, one aspect of the present invention provides an isolated nucleic acid molecule comprising a sequence of nucleotides encoding, or complementary to a sequence encoding, an NAD+ dependent glucocorticoid dehydrogenase enzyme, or a derivative thereof.

In another embodiment, the present invention also provides an isolated DNA molecule comprising a sequence of nucleotides which:
(i) encodes or is complementary to a sequence encoding, an enzyme of mammalian origin having NAD+ dependent glucocorticoid dehydrogenase activity; and
(ii) has at least 40% nucleotide sequence similarity to all or a part thereof the sequence set forth in SEQ ID NO: 1.

In yet another embodiment, the present invention provides an isolated nucleic acid molecule which:
(i) encodes or is complementary to a sequence encoding an NAD+ dependent glucocorticoid dehydrogenase enzyme of mammalian origin; and
(ii) hybridises under low stringency conditions to the nucleotide sequence set forth in SEQ ID NO: 1 or to a complementary strand thereof.

The present invention also provides an oligonucleotide capable of hybridising under low stringency conditions to part of the nucleotide sequence, or to a complement of the nucleotide sequence set forth in SEQ ID NO: 1.

In a second aspect, this invention also provides an isolated polypeptide which comprises an amino acid sequence having the catalytic activity of an NAD+ dependent glucocorticoid dehydrogenase, or a functional mutant, derivative part, fragment, or analogue of said polypeptide. According to this embodiment, the isolated polypeptide of the present invention catalyses the conversion of a glucocorticoid substrate molecule to a receptor inactive 11-dehydro steroid metabolite and has at least 40% amino acid sequence similarity to the amino acid sequence set forth in SEQ ID NO: 2.

In a third aspect, the present invention also provides a method for identifying a modulator of glucocorticoid dehydrogenase enzyme activity which method comprises contacting a reaction mixture comprising a recombinant NAD+ dependent glucocorticoid dehydrogenase polypeptide, and a suitable glucocorticoid substrate, with a chemical compound to be tested and comparing a reaction rate against a reaction rate of said polypeptide in the absence of said chemical compound, and selecting a chemical compound which modulates said enzyme activity.

The present invention also provides a synthetic peptide which is essentially the same, or has at least 40% amino acid sequence similarity to the amino acid sequence set forth in SEQ ID NO: 3.

In yet another aspect, the present invention also provides an antibody that binds to a polypeptide comprising an amino acid sequence which:

(i) has the catalytic activity of an NAD+ dependent glucocorticoid dehydrogenase, or a functional mutant, derivative, part, fragment, or analogue of said polypeptide; or
(ii) is substantially the same as the amino acid sequence set forth in SEQ ID NO: 2, or has at least 40% similarity to all or a part thereof.

Still another aspect of the present invention provides a diagnostic kit for the measurement of the glucocorticoid dehydrogenase antigen level in a human or animal comprising, in a compartmental form, a first compartment adapted to contain an antibody or other immunoreactive molecule that binds specifically to said antigen. Preferably, the kit also contains, a second compartment adapted to contain a specific reference antigen to which the antibody of the first compartment binds, to facilitate quantitation. Further, the kit comprises instructions for use and is packaged ready for use.

BRIEF DESCRIPTION OF THE DRAWINGS

FIG. 6 is a photographic representation showing a western blot of human kidney and placental tissue. Lanes 1 and 2 contain solubilised microsomes from placenta and kidney, respectively. Lanes 3 and 4 contain solubilised 1500 g pellet from placenta and kidney homogenates, respectively. Lanes 5 and 6 contain total homogenates of kidney and placenta, respectively. Lane 7 contains a total homogenate of CHOP cells transfected with pHSD2. One hundred microgram of protein was loaded in each lane.

Figure 1:
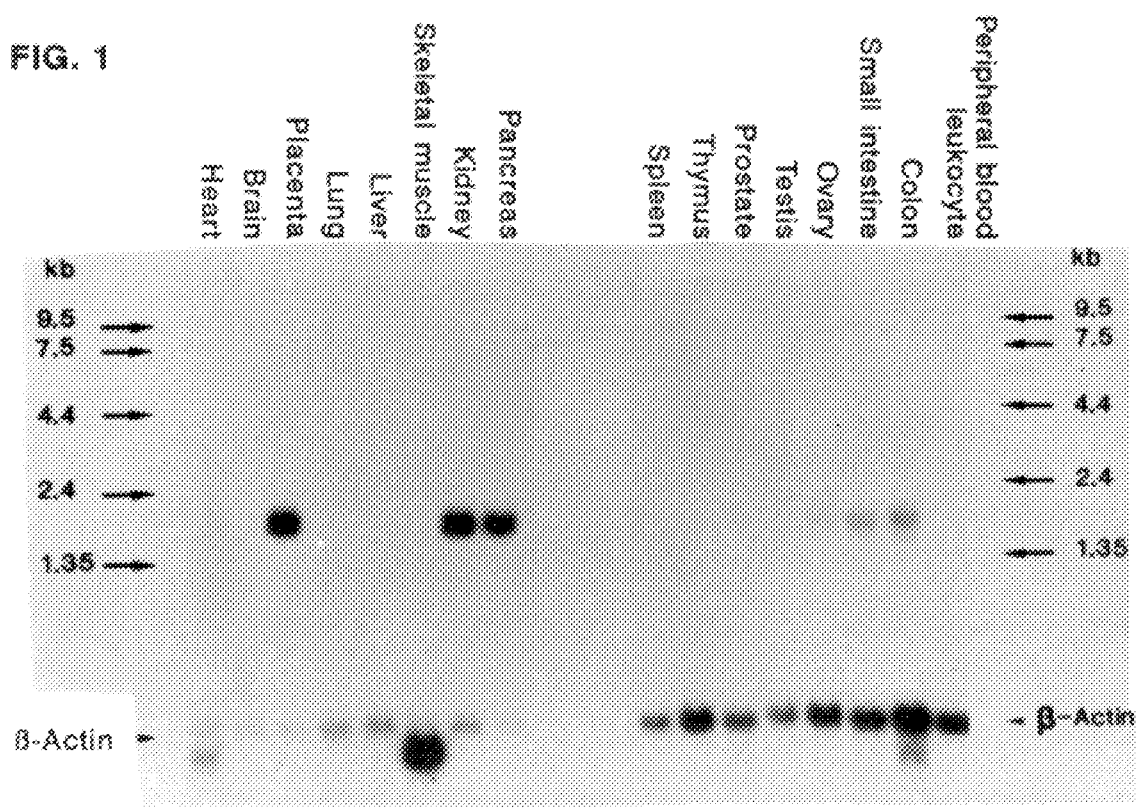
FIG. 1 is a photographic representation of a northern hybridisation showing expression of the 11 βHSD2 gene in 16 different human tissues. The 1.9 kb 11 βHSD2 mRNA band and the control β-actin mRNA band are indicated.

Single letter and three letter abbreviations are used for amino acid residues in the specification, as defined below in Table 1.

TABLE 1

| Amino Acid | Three-letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | T |
| Tyrosine | Tyr | Y |
| Valine | Val | V |

DETAILED DESCRIPTION OF THE PREFERRED EMBODIMENTS

One aspect of the present invention provides a nucleic acid sequence which encodes, or is complementary to a sequence which encodes an NAD+ dependent glucocorticoid dehydrogenase enzyme, or a derivative thereof. Hereinafter the term "NAD + dependent glucocorticoid dehydrogenase" shall refer to a protein which, in the presence of NAD+, enzymatically converts a glucocorticoid to an 11-dehydro metabolite, wherein the metabolite is unable to bind and/or activate a glucocorticoid receptor, or a mineralocorticoid receptor molecule.

Hereinafter the term "glucocorticoid dehydrogenase gene", or similar term shall be used to define a gene which upon expression, enzymatically oxidises a glucocorticoid to an 11-dehydro metabolite, that is unable to bind, or has reduced binding, and/or does not activate a glucocorticoid receptor, or a mineralocorticoid receptor molecule. Reference herein to "genes" is to be taken in its broadest context and includes:

(i) a classical genomic gene consisting of transcriptional and/or translational regulatory sequences and/or a coding region and/or non-translated sequences (i.e. introns, 5'- and 3'- untranslated sequences); or (ii) mRNA or cDNA corresponding to the coding regions (i.e. exons) and 5'- and 3'- untranslated sequences of the gene.

The term "gene" is also used to describe synthetic or fusion molecules encoding all or part of a functional product. Preferred glucocorticoid dehydrogenase genes may be derived from a naturally-occurring glucocorticoid dehydrogenase gene by standard recombinant techniques. Generally, a glucocorticoid dehydrogenase gene may be subjected to mutagenesis to produce single or multiple nucleotide substitutions, deletions and/or additions. Nucleotide insertional derivatives of the glucocorticoid metabolising gene of the present invention include 5' and 3' terminal fusions as well as intra-sequence insertions of single or multiple nucleotides. Insertional nucleotide sequence variants are those in which one or more nucleotides are introduced into a predetermined site in the nucleotide sequence although random insertion is also possible with suitable screening of the resulting product. Deletional variants are characterised by the removal of one or more nucleotides from the sequence. Substitutional nucleotide variants are those in which at least one nucleotide in the sequence has been removed and a different nucleotide inserted in its place. Such a substitution may be "silent" in that the substitution does not change the amino acid defined by the codon. Alternatively, substituents are designed to alter one amino acid for another similar acting amino acid, or amino acid of like charge, polarity, or hydrophobicity.

The present invention extends to the isolated nucleic acid molecule when integrated into the genome of a cell as an addition to the endogenous cellular complement of glucocorticoid dehydrogenase genes.

Another aspect of the present invention is directed to a nucleic acid molecule which comprises a sequence of nucleotides corresponding, or complementary to the sequence as set forth in SEQ ID NO: 1, or having at least about 40%, more preferably at least about 55%, still more preferably at least about 65%, yet still more preferably at least about 75–80% and even still more preferably at least about 85–95% nucleotide similarity to all, or a part thereof, of SEQ ID NO: 1. According to this aspect, said nucleic acid molecule encodes, or is complementary to a sequence encoding, an enzyme of mammalian origin having NAD+ glucocorticoid dehydrogenase activity.

For the purposes of nomenclature, the sequence shown in SEQ ID NO: 1 relates to the human 11 βHSD2 gene, which oxidises glucocorticoids to the corresponding 11-dehydro metabolites. Preferably, the glucocorticoid is cortisol and the 11-dehydro metabolite is cortisone. However the present invention is not limited to this preferred glucocorticoid substrate, and additional glucocorticoid substrates are contemplated, for example corticosterone and the synthetic glucocorticoid dexamethasone, amongst others.

A further aspect of the present invention contemplates a nucleic acid molecule which encodes, or is complementary to a nucleic acid molecule which encodes, or is complementary to a sequence encoding an NAD+ dependent glucocorticoid dehydrogenase enzyme of mammalian origin and which is capable of hybridising under at least low stringency conditions to the nucleic acid molecule set forth in SEQ ID NO: 1, or to a complementary strand thereof.

In one embodiment, the present invention contemplates an oligonucleotide capable of hybridising under low stringency conditions to part of the nucleotide sequence, or to a complement of the nucleotide sequence set forth in SEQ ID NO: 1.

For the purposes of defining the level of stringency, a low stringency is defined herein as being a hybridisation and/or a wash carried out in 6×SSC buffer, 0.1% (w/v) SDS at 28° C. Generally, the stringency is increased by reducing the concentration of SSC buffer, and/or increasing the concentration of SDS and/or increasing the temperature of the hybridisation and/or wash. Conditions for hybridisations and washes are well understood by one normally skilled in the art. For the purposes of clarification, (to parameters affecting hybridisation between nucleic acid molecules), reference is found in pages 2.10.8 to 2.10.16. of Ausubel et al. (1987), which is herein incorporated by reference.

The present invention is particularly directed to a glucocorticoid dehydrogenase gene, preferably 11 βHSD2, encoded by genetic sequences isolated from human organs, and in particular kidney cells. The subject invention clearly contemplates other sources of glucocorticoid dehydrogenase genes, such as but not limited to, other human tissues or organs, other mammalian species including, for example *Rattus sp.*, and cultured cells of human or mammalian origin.

The present invention clearly contemplates a genomic clone equivalent of the nucleotide sequence set forth in SEQ ID NO: 1 and extends to a promoter or functional derivative, part fragment, homologue or analogue thereof from a genomic clone equivalent of the nucleotide sequence defined by SEQ ID NO: 1.

The genetic sequences which encode, or are complementary to genetic sequences which encode, a glucocorticoid dehydrogenase protein may correspond to the naturally occurring sequence or may differ by one or more nucleotide substitutions, deletions and/or additions. Accordingly, the present invention extends to glucocorticoid dehydrogenase genes and any functional genes, mutants, derivatives, parts, fragments, homologues or analogues thereof or non-functional molecules but which are at least useful as, for example, genetic probes, or primer sequences in the enzymatic or chemical synthesis of said gene, or in the generation of immunologically interactive recombinant molecules.

In a particularly preferred embodiment, the glucocorticoid dehydrogenase genetic sequences are employed to identify and isolate similar genes from other human cell, tissue, or organ types, or from the cells, tissues, or organs of another species. According to this embodiment, there is contemplated a method for identifying a related glucocorticoid dehydrogenase genetic sequence, said method comprising contacting genomic DNA, or mRNA, or cDNA with a hybridisation effective amount of a glucocorticoid dehydrogenase genetic sequence, or a functional part thereof, and then detecting said hybridisation.

The related glucocorticoid dehydrogenase genetic sequence may be in a recombinant form, in a virus particle, bacteriophage particle, yeast cell, animal cell, or a plant cell. Preferably, the related genetic sequence is human, or mammalian in origin.

Preferably, the glucocorticoid dehydrogenase genetic sequence (i.e latter genetic sequence) is human in origin. In a most preferred embodiment, the latter genetic sequence is as set forth in SEQ ID NO: 1.

Preferably, the latter genetic sequence is labelled with a reporter molecule capable of giving an identifiable signal (e.g. a radioisotope such as $^{32}$P or $^{35}$S or a biotinylated molecule).

An alternative method contemplated in the present invention involves hybridising a nucleic acid "primer molecule" of at least 10 nucleotides in length to a nucleic acid "template molecule", said template molecule herein defined as a related glucocorticoid dehydrogenase genetic sequence, or a functional part thereof, or its complementary sequence. Specific nucleic acid molecule copies of the template molecule are amplified enzymatically in a polymerase chain reaction, a technique that is well known to one skilled in the art.

Preferably, the nucleic acid primer molecule or molecule which is effective in hybridisation is contained in an aqueous mixture of other nucleic acid primer molecules. More preferably, the nucleic acid primer molecule is in a substantially pure form. In a preferred embodiment, the nucleic acid primer molecule is human, or mammalian in origin. In a most preferred embodiment, the nucleic acid primer molecule is any nucleotide sequence of at least 10 nucleotides in length derived from, or contained within the nucleotide sequence as set forth in SEQ ID NO: 1. According to this embodiment, the nucleic acid primer molecule consists of a combination of any of the nucleotides adenine, cytidine, guanine, thymidine, or inosine, or functional analogues or derivatives thereof, capable of being incorporated into a polynucleotide molecule.

The nucleic acid template molecule may be in a recombinant form, in a virus particle, bacteriophage particle, yeast cell, animal cell, or a plant cell. Preferably, the related genetic sequence originates from a mammalian cell, tissue, or organ. More preferably, the related genetic sequence originates from a human cell, tissue, or organ.

The nucleic acid molecule of the present invention is also useful for developing gene therapies employing antisense or ribozyme molecules, or in co-suppression of the glucocorticoid dehydrogenase gene, in particular the 11 βHSD2 gene. By targetting the endogenous glucocorticoid dehydrogenase gene, expression is diminished, reduced or otherwise lowered to a level that results in reduced metabolism of GC into the 11-dehydro metabolite. A further use is gene therapy employing the use of gene targetting, to replace a non-functional or defective glucocorticoid dehydrogenase gene with a functional copy of the gene sequence.

According to one embodiment there is provided a nucleic acid molecule comprising at least 5 contiguous nucleotide bases capable of hybridising to, or forming a duplex with mRNA encoding a glucocorticoid dehydrogenase enzyme, to reduce translation of said mRNA. This embodiment of the present invention defines primers, probes and other antisense and/or ribozyme molecules capable of instituting or at least reducing translation of said MRNA. Although the preferred antisense and/or ribozyme molecules hybridise to at least about 10 to 20 nucleotides of the target molecule, the present invention extends to molecules capable of hybridising to at least about 50–100 nucleotide bases in length, or a molecule capable of hybridising to a full-length or substantially full-length glucocorticoid dehydrogenase mRNA.

Ribozymes are synthetic RNA molecules which comprise a hybridising region complementary to two regions, each of at least 5 contiguous nucleotide bases in the target mRNA. In addition, ribozymes possess highly specific endoribonuclease activity, which autocatalytically cleaves the target mRNA. A complete description of the function of ribozymes is presented by Haseloff and Gerlach (1988) and contained in International Patent Application No. WO89/05852. The present invention extends to ribozymes which target an mRNA which encodes a glucocorticoid dehydrogenase enzyme.

Co-suppression is the reduction in expression of an endogenous gene that occurs when one or more copies of said gene, or one or more copies of a substantially similar gene are introduced into the cell.

Gene targetting is the replacement of an endogenous gene sequence within a cell by a related DNA sequence to which it hybridises, thereby altering the form and/or function of the endogenous gene and the subsequent phenotype of the cell. According to this embodiment, at least a part of the DNA sequence defined by SEQ ID NO: 1, or a related glucocorticoid dehydrogenase genetic sequence, may be introduced into target cells containing an endogenous glucocorticoid dehydrogenase gene to replace said sequence and/or modify glucocorticoid inactivation.

A yet still further use of a glucocorticoid dehydrogenase genetic sequence is the expression of said gene in plants to confer herbicide resistance properties on the plant. The present invention also extends to a transgenic plant carrying a glucocorticoid dehydrogenase genetic sequence. Generally, the transgenic plant would exhibit increased resistance to a herbicide compound when compared with a non-transgenic plant that is otherwise isogenic. The present invention extends further to the progeny and seed derived from said transgenic plant.

Preferably, the glucocorticoid dehydrogenase genetic sequence is identical or related to the molecule set forth in SEQ ID NO: 1, or a functional derivative, fragment, part, homologue, or analogue thereof and encodes one or more glucocorticoid dehydrogenase polypeptides.

The present invention extends to genetic constructs designed to facilitate expression of a glucocorticoid dehydrogenase genetic sequence which is identical, or complementary to the sequence set forth in SEQ ID NO: 1, or a functional derivative, part, homologue, or analogue thereof, or a genetic construct designed to facilitate expression of an antisense molecule, ribozyme molecule, co-suppression molecule, or gene targetting molecule containing said genetic sequence. Generally, the genetic construct comprises in addition to the subject glucocorticoid dehydrogenase genetic sequence, a promoter and optionally other regulatory sequences designed to facilitate expression of said genetic sequence. The promoter may be derived from a genomic clone encoding a glucocorticoid dehydrogenase enzyme, preferably the human 11 βHSD2 gene, or may be a heterologous promoter from another source. In a preferred embodiment, the promoter is capable of expression in a plant cell. In a particularly preferred embodiment, however, the promoter is capable of expression in a cell which expresses MR and/or GR molecules.

According to this embodiment, one aspect is directed to a genetic construct comprising a promoter or functional derivative, part fragment, homologue, or analogue thereof, from a genomic clone equivalent of the nucleotide sequence defined by SEQ ID NO: 1.

Another aspect of the present invention provides an isolated nucleic acid molecule encoding, or complementary to a nucleic acid molecule encoding, a polypeptide comprising an amino acid sequence substantially as set forth in SEQ ID NO: 2, wherein said polypeptiide is capable of binding to an antibody molecule which interacts immunologically with an NAD+ dependent glucocorticoid dehydrogenase polypeptide, or a functional mutant, derivative, part, fragment, or analogue of same.

In a preferred embodiment the nucleic acid molecule of the present invention encodes, or is complementary to a nucleic acid molecule which encodes, a polypeptide comprising amino acid residues 358–405 inclusive, of the amino acid sequence set forth in SEQ ID NO: 2, wherein said polypeptide is capable of binding to an antibody molecule which interacts immunologically with an NAD+ dependent glucocorticoid dehydrogenase polypeptide, or a functional mutant, derivative, part, fragment, or analogue of same.

Yet another aspect of the present invention provides for the expression of the subject genetic sequence in a suitable host (e.g. a prokaryote or eukaryote) to produce full length or non-full length recombinant glucocorticoid dehydrogenase gene products. Preferably, the polypeptide catalyses the conversion of a glucocorticoid substrate molecule, for example cortisol, corticosterone, or dexamethasone, amongst others, to the corresponding 11-dehydro metabolite product. More preferably, the glucocorticoid dehydrogenase gene product has a sequence that is identical to, or contained within the amino acid sequence set forth in SEQ ID NO: 2.

According to this embodiment, the present invention provides an isolated polypeptide which comprises an amino acid sequence having the catalytic activity of an NAD+ dependent glucocorticoid dehydrogenase, or a functional mutant, derivative part, fragment, or analogue of said polypeptide.

In another embodiment, the present invention provides an isolated polypeptide which:

(i) catalyses conversion of a glucocorticoid substrate molecule to receptor inactive 11-dehydro steroid metabolite; and (ii) has at least 40% amino acid sequence similarity to the sequence set forth in SEQ ID NO: 2.

In a related embodiment, the present invention provides a "sequencably pure" form of the amino acid sequence set forth in SEQ ID NO: 2. "Sequencably pure" is hereinbefore described as substantially homogeneous to facilitate amino acid determination. In a further related embodiment, the present invention provides a "substantially homogeneous" form of the amino acid sequence set forth in SEQ ID NO: 2, wherein the term "substantially homogeneous" is hereinbefore defined as being in a form suitable for interaction with an immunologically interactive molecule. Preferably, the polypeptide is at least 20% homogeneous, more preferably at least 50% homogeneous, still more preferably at least 75% homogeneous and yet still more preferably at least about 95–100% homogenous, in terms of enzyme activity per microgram of total protein in the protein preparation.

The present invention extends to the 3-dimensional structure of the polypeptide defined by the amino acid sequence set forth in SEQ ID NO: 2, or a functional derivative, analogue, or a part thereof. The 3-dimensional structure of the 11 βHSD2 enzyme is of particular use in designing molecules that interact and modify the activity of said enzyme.

The present invention also extends to a synthetic peptide comprising any part of the amino acid sequence set forth in SEQ ID NO: 2, or having at least 40% similarity to all or a part thereof, wherein the amino acid sequence set forth in SEQ ID NO: 2 is an NAD+ dependent glucocorticoid dehydrogenase polypeptide.

The full-length recombinant polypeptide, or synthetic polypeptide, or an enzymatically active part thereof is useful in the production of 11-dehydro steroid compounds from glucocorticoid precursor molecules. In one embodiment, a genetic construct is used to express a recombinant glucocorticoid dehydrogenase polypeptide in a bacterial, yeast, human, or other mammalian cell, referred to hereinafter as a host cell, in the presence of a glucocorticoid substrate molecule. Preferably, the glucocorticoid substrate molecule is cortisol, corticosterone, or dexamethasone. The recombinant glucocorticoid dehydrogenase of the present invention enzymatically converts said substrate molecule into the corresponding 11-dehydro metabolite, which may be isolated by disruption of the host cell, and/or subsequent purification. Methods for purification of said 11-dehydro metabolite will be well known to one of ordinary skill in the art, and include various chromatographic procedures, for example reverse phase chromatography, ion-exchange chromatography and hydrophobic interaction chromatography, amongst other procedures.

The recombinant glucocorticoid dehydrogenase gene product, or part fragment, functional derivative, synthetic peptide, or 3-dimensional structure thereof, is also used to produce immunologically interactive molecules, such as antibodies, or functional derivatives thereof, for example Fabs, SCABS (single-chain antibodies), or antibodies conjugated to an enzyme, radioactive or fluorescent tag, the only requirement being that the recombinant products are immunologically interactive with antibodies to all, or part, or a glucocorticoid dehydrogenase gene product.

According to this aspect, the present invention provides an antibody that binds to a polypeptide comprising an amino acid sequence which:

(i) has the catalytic activity of an NAD+ dependent glucocorticoid dehydrogenase, or a functional mutant, derivative, part, fragment, or analogue of said polypeptide; or (ii) is substantially the same as the amino acid sequence set forth in SEQ ID NO: 2, or has at least 40% similarity to all or a part thereof.

In a particularly preferred embodiment, the present invention provides an antibody that binds a polypeptide comprising an amino. acid sequence which is substantially the same, or at least 40% similar to an amino acid sequence comprising amino acid residues 358–405 of SEQ ID NO: 2.

Antibodies to a recombinant NAD+ dependent glucocorticoid dehydrogenase gene product are particularly useful in screening patients to determine sites and quantitative levels of said gene product in a biological sample. The biological sample may be a biopsy originating from skin, renal, ovarian, placental, intestinal, pancreatic, or colonic tissue, amongst others. Preferably, the biological sample is from a tissue which expresses MR or GR molecules. The results of said screen may be applied to diagnosis of the hypertensive condition of a patient, or indicate a predisposition to hypertension, and/or a possible cause of hypertension in a patient. Additionally, the results of said screen may be used to indicate the possible success of an in vitro fertilisation and embryo transfer protocol in a patient.

According to this aspect, the present invention contemplates a diagnostic kit for the measurement of the amount of an NAD+ dependent glucocorticoid dehydrogenase antigen in a human or animal, comprising in compartmental form a first compartment adapted to contain an antibody preparation that binds specifically to said antigen.

Such antibodies may be monoclonal or polyclonal and may be selected from naturally occurring antibodies to an epitope of a glucocorticoid dehydrogenase gene product or may be specifically raised to a recombinant glucocorticoid dehydrogenase gene product. In the case of the latter, the gene product may need to first be associated with a carrier molecule. Alternatively, fragments of antibodies may be used such as Fab fragments. Furthermore the present invention extends to recombinant and synthetic antibodies and to antibody hybrids. A "synthetic antibody" is considered herein to include fragments and hybrids of antibodies. The antibodies and recombinant gene products of the present invention are particularly useful for the immunological screening of glucocorticoid dehydrogenase activity in a cell, as a diagnostic for hypertension and in predicting outcomes of an in vitro fertilisation (IVF) regime.

It is within the scope of this invention to include any second antibodies (monoclonal, polyclonal or fragments of antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of a recombinant glucocorticoid dehydrogenase gene product.

Both polyclonal and monoclonal antibodies are obtainable by immunisation with a recombinant glucocorticoid dehydrogenase gene product, or a functional derivative, or part thereof, and either type is utilisable for immunoassays. The methods of obtaining both types of sera are well known in the art. Polyclonal sera are less preferred but are relatively easily prepared by injection of a suitable laboratory animal with an effective amount of recombinant or 11 βHSD gene product, or antigenic or immunointeractive parts thereof, collecting serum from the animal and isolating specific sera by any of the known immunoadsorbent techniques. Although antibodies produced by this method are utilisable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitised against the immunogenic preparation can be done by techniques which are well known to those who are skilled in the art (see, for example, Douillard and Hoffman, 1981; Kohler and Milstein, 1975; Kohler and Milstein, 1976).

Determination of the presence of a glucocorticoid dehydrogenase gene product in a cell or cell extract may be accomplished in any number of ways, including but not limited by western blotting, ELISA and RIA procedures. A wide range of immunoassay procedures are available as can be seen by reference to U.S. Pat. Nos. 4,016,043 4,424279 and 4,018,653. These include both single-site and two-site or "sandwich" assays of the non-competitive type, as well as traditional competitive binding assays. These assays also include direct binding of labelled antibody to a target.

Sandwich assays are among the most useful and commonly used assays and are favoured for use in the present invention. A number of variations of the sandwich assay exist, and all are intended to be encompassed by the present invention. Briefly, an unlabelled antibody is immobilised on a solid support and the sample to be tested is brought into contact with the bound molecule. After a suitable incubation period, sufficient to all formation of an antibody-antigen complex, a second antibody specific to the antigen, labelled with a reporter molecule capable of producing a detectable signal is then added and incubated, allowing sufficient time for the formation of a complex of antibody-antigen-labelled antibody. Any unreacted material is washed away and the presence of the antigen is determined by observation of a signal produced by the reporter molecule.

In this case, the first antibody is raised against a glucocorticoid dehydrogenase polypeptide, or functional derivative, or part thereof. Preferably the glucocorticoid dehydrogenase is the 11 βHSD2 polypeptide, more preferably the human 11 βHSD2 peptide. Even more preferably, the antibody is raised against the polypeptide fragment set forth in SEQ ID NO: 3. The polypeptide fragment may contain an additional N-terminal cysteine, in the case of a synthetic peptide, to facilitate coupling to a carrier molecule. Preferably, the carrier molecule is keyhole limpet hemocyanin.

The antigen is a glucocorticoid dehydrogenase polypeptide, or a functional derivative, or part thereof. Preferably the antigen is 11 βHSD2, or more preferably human 11 βHSD2, or a functional derivative, or a part thereof. Even more preferably, the antigen is the amino acid sequence set forth in either SEQ ID NO: 2, or SEQ ID NO: 3.

The results may be qualitative, by simple observation of the visible signal, or quantitative, by comparing the signal obtained with a control signal obtained by using known amounts of purified antigen. Variations in the assay may include a simultaneous assay in which both the sample and labelled antibody are added simultaneously to the bound antibody. These techniques are well known to those skilled in the art, including any minor variations as will be readily apparent. In accordance with the present invention, the sample is one which might contain MR or GR and glucocorticoid dehydrogenase activity, for example the colon, kidney, hippocampus, placenta, or gonads.

In the typical sandwich assay, the first antibody is bound to a solid support either covalently, or passively, for example via van der Waals interactions. The solid surface is typically either glass or a polymer, the most commonly used polymers being cellulose, polyacrylamide, nylon, polystyrene, polyvinyl chloride or polypropylene. The solid supports may be in the form of tubes, beads, discs, microplates, membranes or any other surface suitable for conducting an immunoassay. The binding processes are well-known in the art and generally consist of cross-linking, covalent binding or physical adsorption. The polymer-antibody complex, once formed is washed to remove unbound antibody. Polymer sites that have not formed a complex with the antibody are then protected by incubation with a protein solution, for example serum albumin. An aliquot of the sample to be tested is then added to the solid phase complex and incubated for a sufficient period of time (e.g. 20–40 minutes) and under suitable conditions (e.g. 25° C.) to allow binding of any antigen present in the sample to the antibody. Following the incubation period, the reaction locus is washed and dried and incubated with a second antibody specific for a portion of the first antibody. The second antibody is linked to a reporter molecule which is used to indicate the binding of the second antibody to the hapten.

An alternative method involves immobilising the target molecules in the biological sample and then exposing the immobilised target to specific antibody which may or may not be labelled with a reporter molecule. Depending on the amount of target and the strength of the reporter molecule signal, a bound target may be detected by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide-containing molecules (i.e. radioisotopes) and chemiluminescent molecules.

In the case of an enzyme immunoassay, an enzyme is conjugated to the second antibody, generally by means of glutaraldehyde or periodate. As will be readily recognised, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates which yield a fluorescent product rather than the chromogenic substrates noted above. In all cases, the enzyme-labelled antibody is added to the first antibody-hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. The term "reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. As in enzyme immunoassays (EIA), the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

It will be readily apparent to the skilled technician how to vary the above assays and all such variations are encompassed by the present invention.

A further aspect of the present invention contemplates a method of determining the sites and levels of transcription of a glucocorticoid dehydrogenase gene in a cell. According to this embodiment, RNA is extracted from a cell and used as a template to synthesise cDNA, using a reverse transcriptase enzyme. Primers of at least 12 nucleotides in length are designed and synthesised that are complementary to one or more regions of the subject sequence and/or its complement. Said primers are then hybridised to the cDNA and glucocorticoid dehydrogenase genetic sequences are amplified using polymerase chain reaction. In this embodiment, the level of DNA product amplified is proportional to the level of mRNA transcript in the cell which encodes a glucocorticoid dehydrogenase. Preferably, the target cell from which DNA is amplified, expresses MR and/or GR molecules, for example kidney, placenta, prostate, gonads, small intestine and colon, amongst others.

In a particularly preferred embodiment, the glucocorticoid dehydrogenase genetic sequence is the sequence set forth in SEQ ID No: 1, or its complement, or a functional derivative, fragment, or a part thereof.

Another aspect of the present invention contemplates a method for identifying a modulator of glucocorticoid dehydrogenase enzyme activity which method comprises contacting a reaction mixture comprising a recombinant NAD+ dependent glucocorticoid dehydrogenase polypeptide, and a suitable glucocorticoid substrate, with a chemical compound to be tested and comparing a reaction rate against a reaction rate of said polypeptide in the absence of said chemical compound, and selecting a chemical compound which modulates said enzyme activity.

More particularly, the method comprises the expression, in a cell, of a genetic construct comprising a gene encoding a glucocorticoid dehydrogenase polypeptide operably linked to a promoter sequence. A basal activity level for the glucocorticoid dehydrogenase polypeptide is established by measuring conversion of a glucocorticoid to the 11-dehydro metabolite in the presence of said glucocorticoid substrate molecule and a cofactor, particularly NAD+. The activity of said polypeptide is also measured in the presence of one or more chemical compounds which are potential agonists or antagonists, of glucocorticoid metabolism, in addition to the reaction mixture used to determine the basal activity level. The activity of the glucocorticoid dehydrogenase polypeptide is then compared in the absence and presence of the chemical compound which is a potential agonist or antagonist of glucocorticoid metabolism.

The cell may be a bacterial, yeast, plant or animal cell. In a preferred embodiment, the cell is a mammalian cell, more preferably a human cell.

The substrate molecule may be, but is not limited to cortisol, corticosterone, or dexamethasone. In a preferred embodiment, the substrate glucocorticoid molecule is labelled with a radioactive, or a fluorescent tag. The present invention extends to other means of labelling the substrate molecule.

Preferably, the potential agonist or antagonist of glucocorticoid metabolism is an agonist, or antagonist of 11 βHSD2 enzyme activity. An example of an antagonist of 11 βHSD2 activity is glycyrrhetinic acid, amongst others.

The present invention is further described in the following Examples. The embodiments exemplified hereinafter are in no way to be taken as limiting the subject invention.

EXAMPLE 1

Cell Culture

Experiments were conducted in CHOP-C4 cells (Heffernan and Dennis, 1991) grown in RPMI 1640 medium.

EXAMPLE 2

Isoation of a cDNA Clone Encoding a glucocorticoid dehydrogenase 11 βHSD2 cDNA was constructed from female human kidney poly (A)$^+$ mRNA and cloned directionally behind the cytomegalovirus promoter in the mammalian expression vector pcDNA1 (Clontech Laboratories, Inc., CA). Recombinant plasmid DNA was transfected into *Eschernchia coli* MC1062/P3 cells as follows: 2 μl of plasmid was added to 40 μl of competent MC1062/P3 cells and the mixture electroporated (at 200Ω, 25 μFD). DNA was purified by alkaline lysis. CHOP cells were transfected with 98 pools of 5000 clones per pool as described by Heffernan and Dennis (1991). Transfected cells were incubated for 48 hours, after which time 150,000 cpm of [$^3$H]corticosterone was added to the culture medium and incubated overnight with the cells. Culture medium was then extracted and steroid metabolites assayed by thin layer chromatography (TLC), with a solvent mixture of ethanol/chloroform [8:92 (v/v)], to identify [$^3$H] 11-dehydrocorticosterone. A single plasmid pHSD2 was isolated from a positive plasmid pool by sibling selection.

EXAMPLE 3

Nucleotide Sequence Analysis of Plasmid pHSD2

Sequence analysis of the insert of pHSD2 revealed an insert of 1881 nucleotides. The sequenced region of pHSD2 contains a single reading frame from nucleotides 109 to 1323 inclusive, encoding a polypeptide of 405 amino acid residues.

Multiple sequence alignment showed that pHSD2 encodes a new member of the short chain alcohol dehydrogenase (SCAD) superfamily. The amino acid sequence set forth in SEQ ID NO. 2 contains 5 domains that are highly conserved within the SCAD superfamily, between amino acid residues 82 to 111, 160 to 169, 212 to 222, 232 to 249, and 254 to 269 inclusive. The human 11 βHSD2 polypeptide is 90% identical over the first 357 amino acid residues, to the postulated sequence of the sheep 11 βHSD2 protein (Agarwal et al., 1994). Amino acid residues 358 to 405 show no sequence homology, however, to the published sheep polypeptide (Agawarl et al., 1994). Further, the polypeptide encoded by pHSD2 is only 35% identical to the NAD+ dependent rat 17β-hydroxysteroid dehydrogenase type 2 enzyme (Wu et al., 1993) at the amino acid level. The polypeptide encoded by pHSD2 has only 14% identity with the rat 11 βHSD1 enzyme (Agarwal et al., 1989). Further, the polypeptide encoded by pHSD2 has an estimated molecular weight of 44.14 kDa and contains one potential N-linked glycosylation site.

EXAMPLE 4

Tissue Specific Distribution of 11 βHSD2 mRNA

Poly(A)$^+$ RNA (2 μg) was electrophoresed on a 1.2% (w/v) agarose gel containing formaldehyde, transferred to a nylon membrane by Northern blotting and fixed by UV irradiation. RNA was hybridised to the $^{32}$P labelled cDNA insert from pHSD2 as described by Krozowski et al. (1990).

Following hybridisation, mRNA encoding 11 βHSD2 was clearly detectable in a range of human tissues including the placenta, kidney, pancreas, prostate, ovary, small intestine and colon (FIG. 1). Low levels of 11 βHSD2 mRNA were also detectable in the spleen and testis. There was no detectable mRNA in preparations from human heart, brain, lung, liver, skeletal muscle, thymus, or peripheral blood leucocytes. Thus, expression of the 11 βHSD2 gene is restricted to mineralocorticoid target tissues and the prostate, gonads and spleen.

The detection of 11 βHSD2 mRNA in the human pancreas is consistent with the observation in rats, that the pancreas contains 11 βHSD enzyme activity that is immunologically distinct from the rat 11 βHSD1 polypeptide (Monder, 1991). Consistent with expression of the 11 βSD2 gene in the pancreas, pancreatic intercalated and interlobular ducts contain mineralocorticoid receptors (Sasano et al., 1992), and aldosterone appears to be involved in regulating amylase levels in pancreatic exocrine cells (Alliet et al., 1989). Thus 11 βHSD2 activity may protect the mineralocorticoid receptor in cells of the pancreatic intercalated and interlobular ducts, and may modulate electrolytes in pancreatic exocrine fluid.

EXAMPLE 5

Analysis of Enzyme Activity

CHOP cells were transfected with plasmid pHSD2, which contains an insert encoding 11 βHSD2. After 60 hours incubation in 85 mm plates, cellular homogenates were prepared and assayed for their ability to metabolise glucocorticoid substrates in the presence of 1 mM NAD+, or 1 mM NADP+. Confluent cells were homogenised in 1 ml of homogenisation buffer (0.25M sucrose, 10 MM phosphate, pH 7). Reaction mixtures (500 μl) contained either 40 μl of homogenate plus [$^3$H]corticosterone, or 80 μl of homogenate plus [$^3$H]cortisol, or 120 μl of homogenate plus [$^3$H] dexamethasone, in homogenisation buffer. All reactions contained 1–2 nM tritiated glucocorticoid substrate plus 10 nM unlabelled glucocorticoid substrate. Reaction mixtures were incubated at 37° C. for 40 minutes and steroid metabolites were assayed by thin layer chromatography. Phosphoimager (Fuji, Inc) scanning of TLC plates showed a single 11-dehydro metabolite in each case.

Figure 2A:
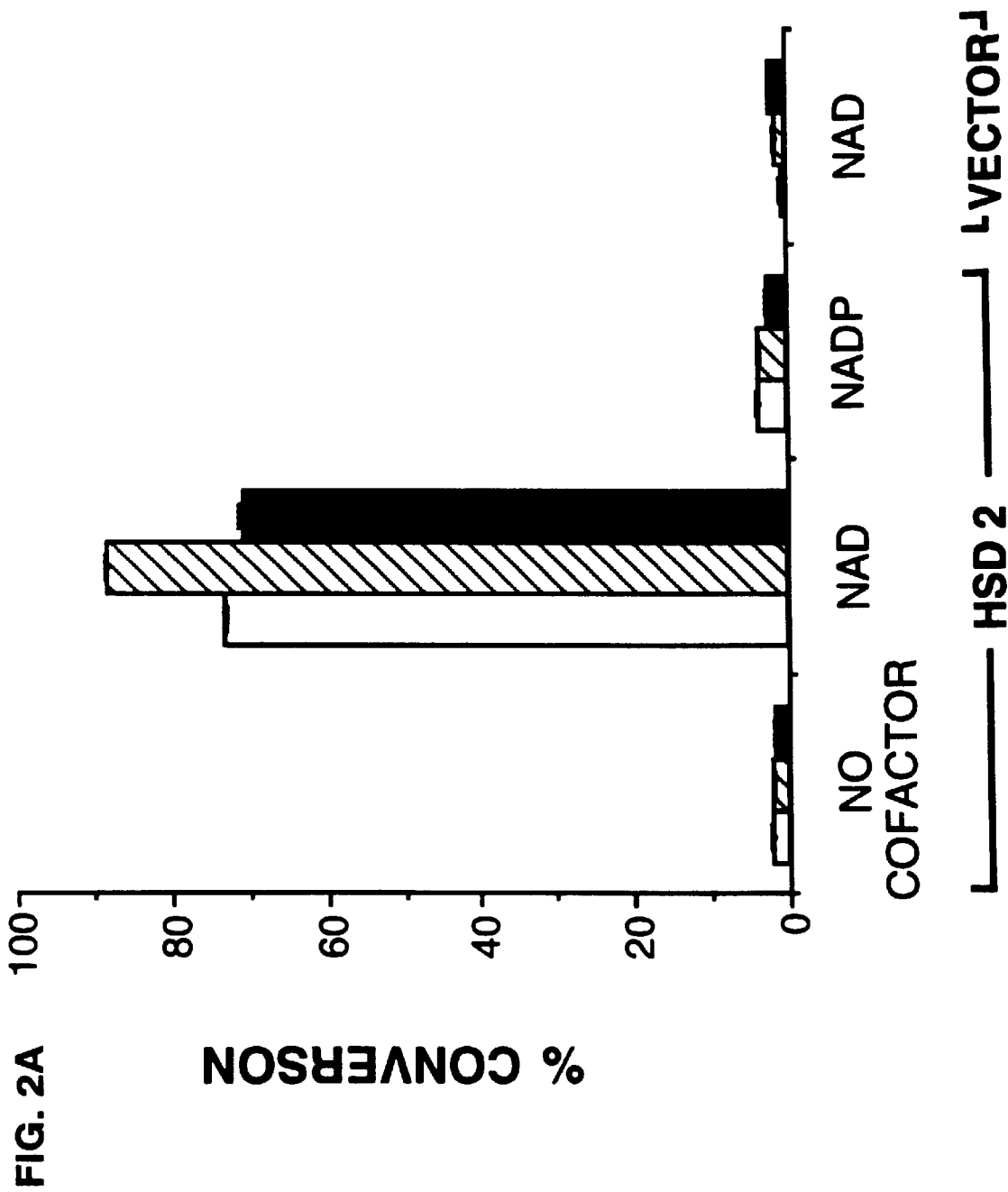
FIG. 2 is a graphical representation showing (a)cofactor specificity and (b) directionality and end-product inhibition of 11 βHSD2. In panel (a), reaction mixtures were supplied with [$^3$H]corticosterone (open bars), [$^3$H]cortisol (hatched bars), or [$^3$H]dexamethasone (solid bars). In panel (b), reaction mixtures were supplied with (I) [$^3$H]cortisone (open bar) or 11-[$^3$H]dehydrocorticosterone (hatched bar); (II)[$^3$H]cortisol (open bar) or [$^3$H]corticosterone (hatched bar); (III) [$^3$H]cortisol plus 1 μM unlabelled cortisone (open bar) or [$^3$H]corticosterone plus 1 μM unlabelled 11-dehydrocorticosterone (hatched bar). Error bars indicate standard deviations.

Homogenates of pHSD2 transfected CHOP cells incubated with corticosterone, cortisol, or dexamethasone, only showed significant glucocorticoid metabolism when NAD+, but not NADP+, was included as a cofactor (FIG. 2a). The ability of the polypeptide encoded by pHSD2 to metabolise the synthetic glucocorticoid dexamethasone and the NAD+ cofactor specificity of this polypeptide, are consistent with the identification of pHSD2 as a cDNA encoding 11 βHSD2 enzyme activity.

Figure 2B:
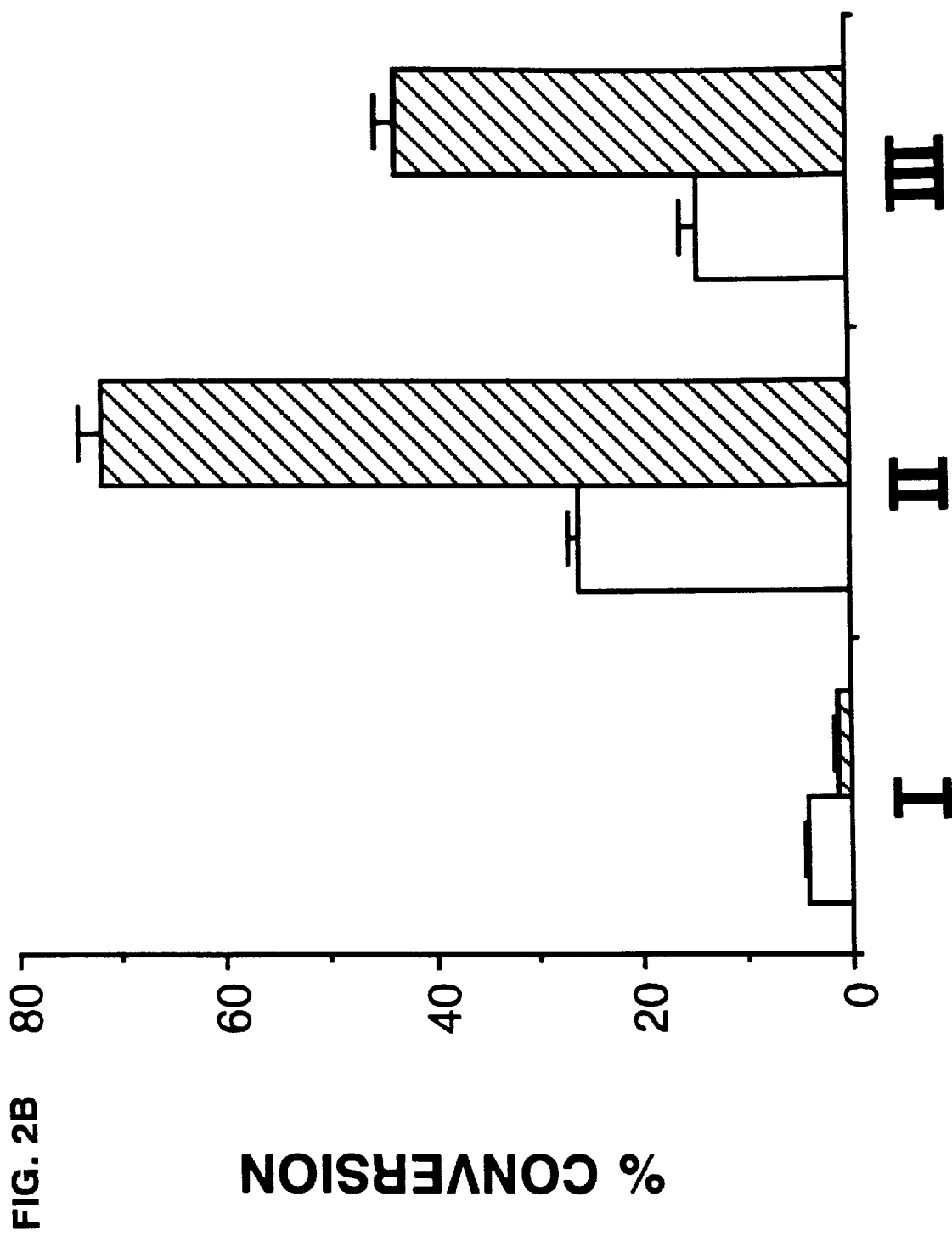

To determine directionality and extent of end production inhibition of the enzyme encoded by pHSD2, monolayer cultures of transfected CHOP cells were incubated for 1.5 hours at 37° C. with 1–2 nM labelled substrates plus 10 nM corresponding unlabelled 11-dehydro metabolite (FIG. 2b). The culture medium was then removed, extracted and assayed by TLC for the presence of the 11-dehydro metabolite.

Intact transfected CHOP cells converted corticosterone and cortisol to the receptor inactive metabolites, 11-dehydro corticosterone, and cortisone, respectively (FIG. 2b). FIG. 2b (II) shows that the enzyme is capable of metabolising cortisol and corticosterone. In contrast, there is no metabolite formed when transfected CHOP cells are incubated with labelled cortisone or 11-dehydro corticosterone (FIG. 2b I). These results suggest that the enzyme encoded by pHSD2 acts unidirectionally uniquely as a dehydrogenase in intact mammalian cells, consistent with previous studies indicating that the NAD+ dependent 11 βHSD2 enzyme is essentially totally dehydrogenase in directionality (Naray-Fejes-Toth et al., 1991). Dehydrogenase activity was also estimated in the presence of an excess of the respective 11-dehydro metabolite (FIG. 2b, III). Consistent with previous studies (Rusvai and Naray-Fejes-Toth, 1993), the cloned dehydrogenase shows inhibition of enzyme activity in the presence of high concentrations of reaction end product.

EXAMPLE 6

Kinetics of 11 β hydroxysteroid dehydrogenase 2 Enzyme Activity

To determine the $K_m$ values of 11 βHSD2 for the glucocorticoid substrate corticosterone, aliquots of transfected CHOP cell homogenates (33 µl) were incubated for 5 minutes at 37° C. with 2.2 nM [$^3$H]corticosterone and 0.7–50 nM unlabelled corticosterone. The $K_m$ value of the enzyme for the glucocorticoid substrate cortisol, was determined by incubating homogenates (50 µl) with 1.9 nM [$^3$H] cortisol and 25–200 nM unlabelled cortisol.

Figure 3A:
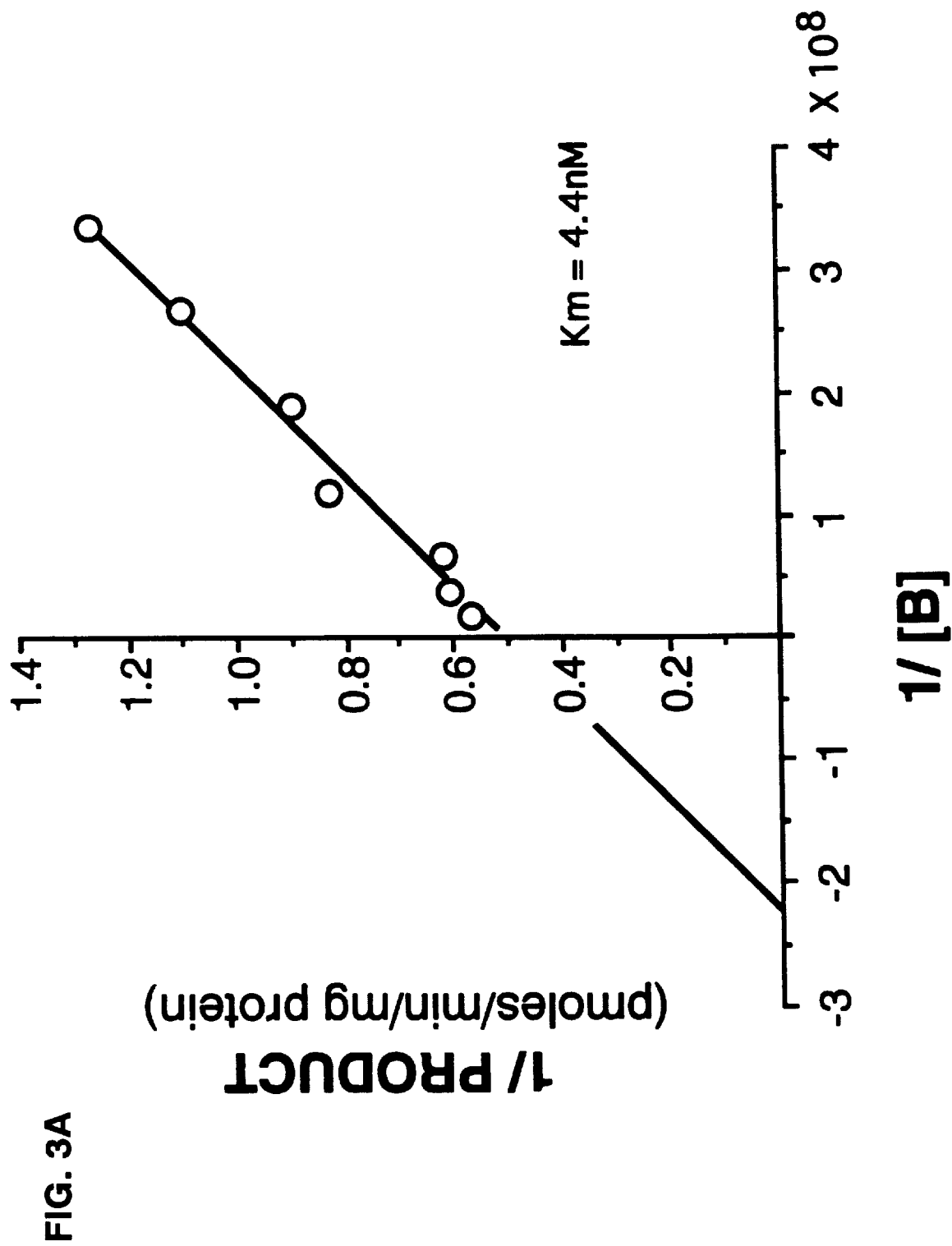
FIG. 3 is a graphical representation showing the Km values of 11 βHSD2 for (a) corticosterone and (b) cortisol. Error bars indicate standard deviations.
Figure 3B:
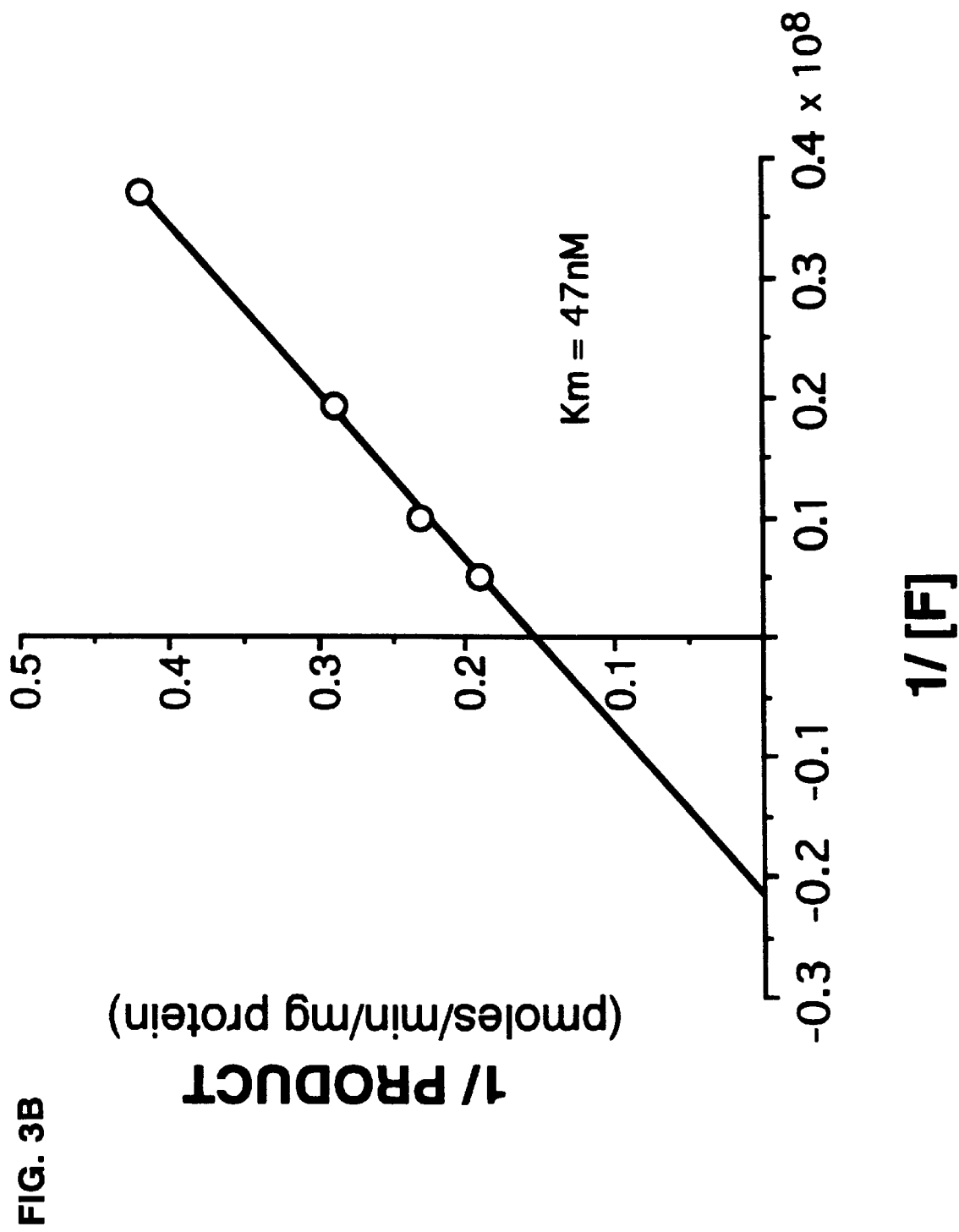

Double reciprocal plot analysis of homogenates of pHSD2 transfected CHOP cells showed a $K_m$ value of 4.4±1.2 nM (mean±SD, n=3) for corticosterone (FIG. 3a). The enzyme encoded by pHSD2 similarly has a $K_m$ value for cortisol of 47±1.8 nM (means±SD, n=3) in homogenates of transfected CHOP cells (FIG. 3b). Measured $K_m$ values are in excellent agreement with $K_m$ values obtained for 11 βHSD2 enzyme activity in human fetal kidney tissue (Stewart et al., 1994) and in rabbit cortical collecting duct cells (Nary-Fejes-Toth et al., 1993), and with the purified placental 11 βHSD2 enzyme (Brown et al, 1993). The nanomolar affinity of the polypeptide encoded by HSD2 for glucocorticoid substrates, suggests the enzyme is effective in reducing intracellular glucocorticoids to levels which will affect mineralocorticoid receptor and glucocorticoid receptor activation, and is therefore an effective modulator of hormone action. The efficiency of the dehydrogenase may be further increased by mechanisms such as intracellular compartmentalisation of the enzyme.

EXAMPLE 7

Inhibition of Enzyme Activity by glycyrrhetinic Acid

CHOP cells were transfected with pHSD2 and, after 60 hours, cellular homogenates were assayed for their ability to metabolise cortisol in the presence of glycyrrhetinic acid. CHOP cell homogenates (30 µl) prepared as described in Example 5, were incubated with 30 minutes at 37° C. with 2 nM [$^3$H]cortisol plus 10 nM unlabelled cortisol and up to 1 µmol glycyrrhetinic acid.

Figure 4:
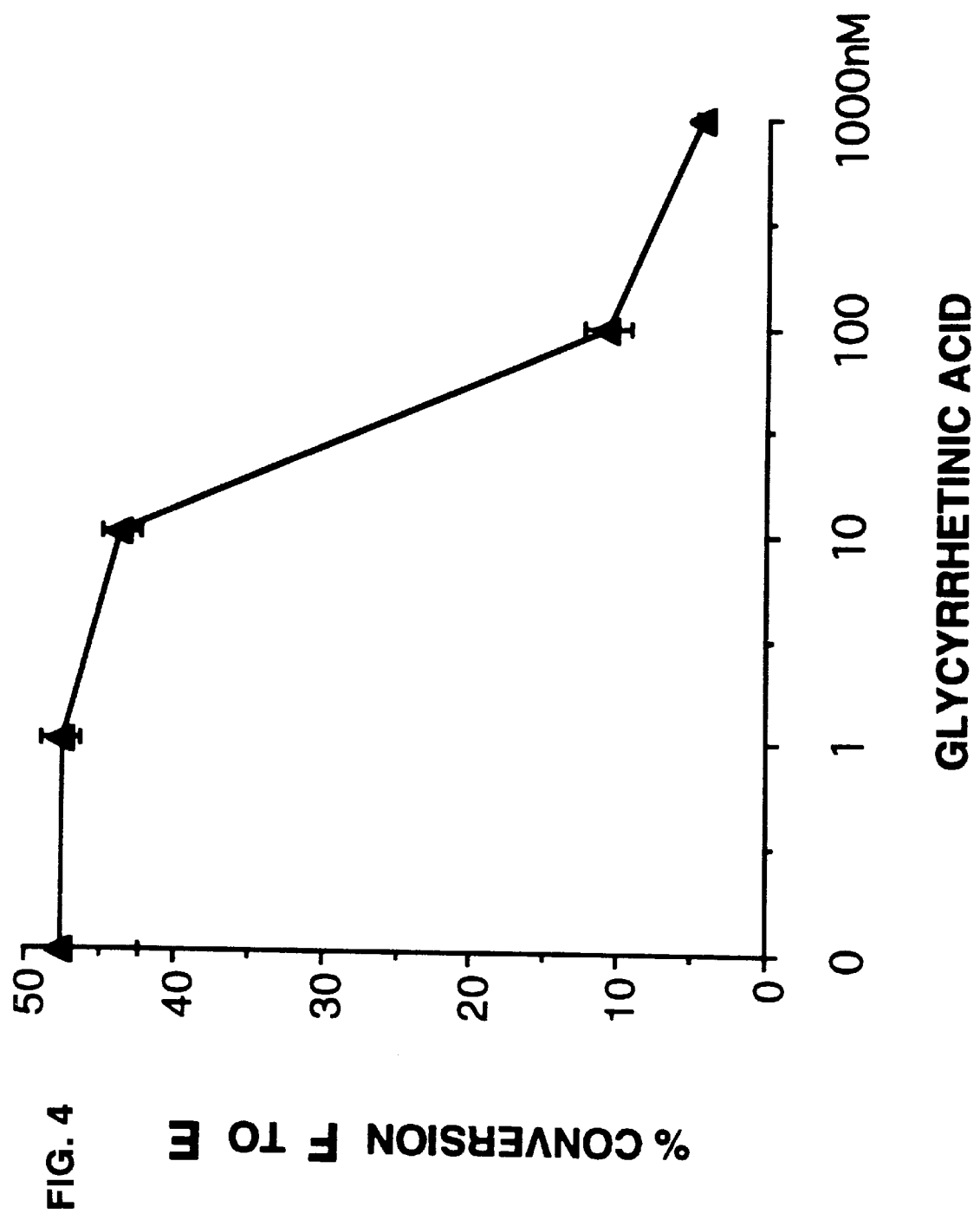
FIG. 4 is a graphical representation showing glycyrrhetinic acid inhibition of [$^3$H]cortisol metabolism by 11 βHSD2. Error bars indicate standard deviations.

As shown in FIG. 4, glycyrrhetinic acid potently inhibits cortisol metabolism by homogenates of CHOP cells transfected with pHSD2. Together with determinations of the substrate and cofactor specificity (FIG. 2a), directionality and end product inhibition of the enzyme (FIG. 2b), in addition to measured $K_m$ values of the enzyme for glucocorticoid substrates (FIG. 3), these data indicate that the polypeptide encoded by pHSD2 is 11 βHSD2.

EXAMPLE 8

Synthetic Peptide and Anti-peptide Antibody Production

A peptide corresponding to the C-terminus of the 11 βHSD2 protein (amino acid residues 388–405 inclusive) having the amino acid sequence set forth in SEQ ID NO: 3, was synthesised, purified by reverse-phase HPLC, and characterised by mass spectometry (Chiron Mimotopes, Clayton, Australia). The peptide contained an N-terminal cysteine residue to facilitate coupling to a keyhole limpet hemocyanin (Sigma, St Louis, Mo.) with m-naleimidobenzoyl-N-hydroxysuccinimnide (Pierce, Rockford, Ill.). The coupling reaction was essentially as described by Lerner et al. (1981). Antibodies were prepared against the synthetic peptide by a standard protocol (Berndt et al., 1985a). Antipeptide IgG was affinity purified on peptide coupled to a 1:1 mixture of Affi-gel 10 and 15 (0.5 mg peptide/5 ml resin and 0.5 mg peptide conjugated to BSA/5 ml resin) according to the manufacturer's instructions (Bio-Rad, Richmond, Calif.). Non-immune rabbit IgG was prepared as described by Berndt et al. (1985a, b).

EXAMPLE 9

Western Blot Analysis

CHOP cells were transfected with pcDNA1 vector or with pHSD2 and cells were grown for 2–3 days at 37° C. Total cell homogenates were prepared by homogenisation in 1 ml of homogenisation buffer (0.25 mol sucrose, 10 mmol phosphate, pH 7). Total tissue homogenates were also prepared from frozen human placenta and kidney tissue by homogenisation in 5 volumes (w/v) of phosphate-buffered saline solution. The total homogenate was clarified by centrifugation at 1500 g for 1 minute (4° C.). Microsomes were recovered from the supernatants by further centrifugation at 100,000 g for 1 hour (4° C.). Pellets were dissolved by boiling in 10% (w/v) SDS solution. Protein samples (100 µg) were loaded onto SDS-polyacrylamide gels, blotted onto membranes and probed with anti-peptide IgG. Bound antibodies were detected using horseradish peroxidase-conjugated anti-(rabbit IgG) immunoglobulin. Procedures for gel electrophoresis and western blotting were essentially as described by Berndt et al. (1985a).

Figure 5:
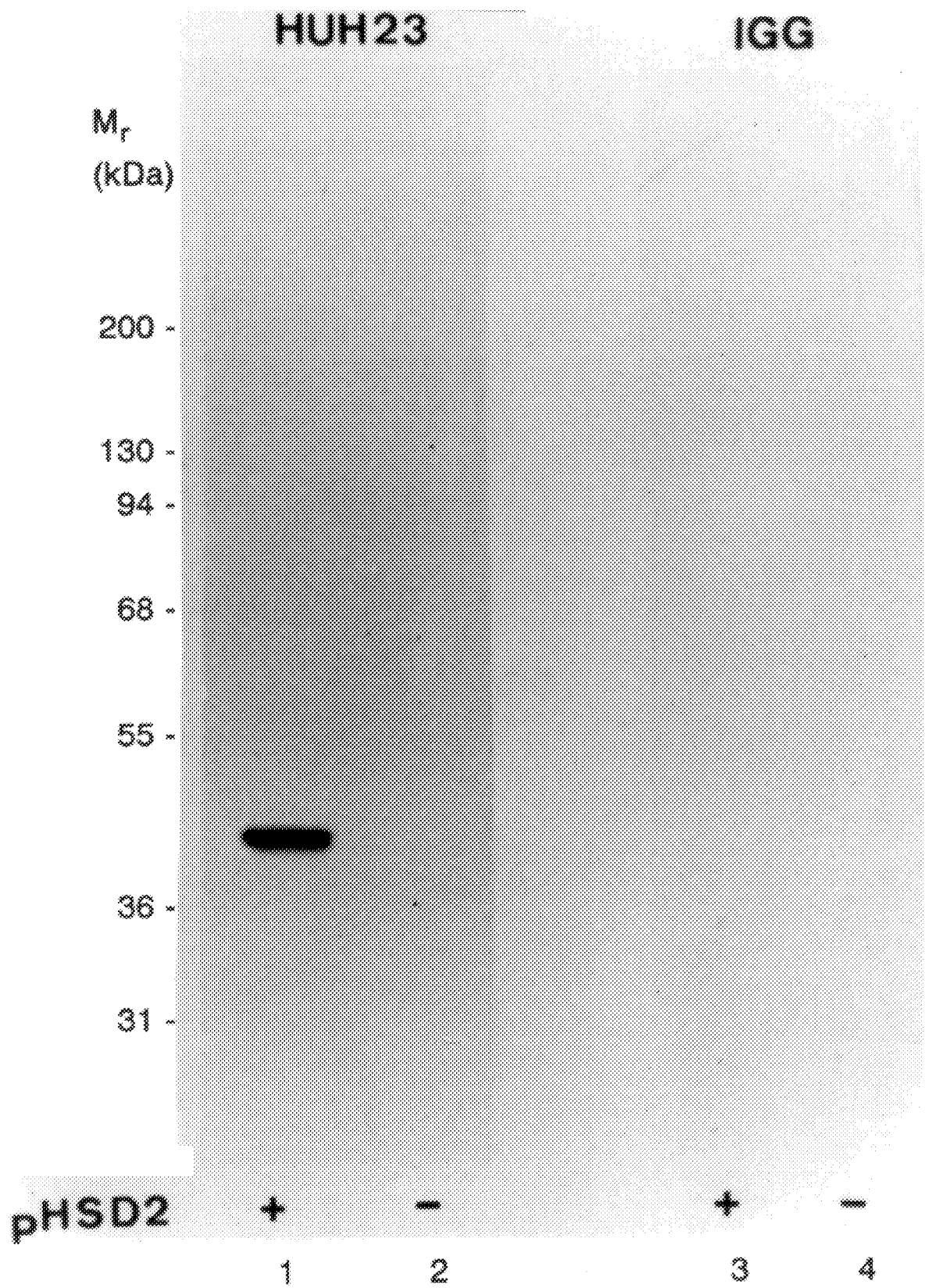
FIG. 5 is a photographic representation showing a western blot analysis of pHSD2-transfected CHOP cells. Lanes 1 and 3 contain total homogenates of transfected CHOP cells. Lanes 2 and 4 contain untransfected CHOP cells. Lanes 1 and 2 were probed with anti-peptide IgG, Lanes 3 and 4 were probed with Preimmune serum.

As shown in FIG. 5, when CHOP cells were transfected with pHSD2 and homogenates analysed by Western blot analysis a single band was observed at 41,000 daltons (FIG. 5, lane 1). In contrast, cells transfected with the pcDNAI vector alone did not display detectable immunoreactivity on Western blot analysis (FIG. 5, lane 2) and no signal was detected when pre-immune serum was used to probe identical blots (FIGS. 5, lanes 3 and 4). Thus, the anti-peptide IgG is specific for the 11 βHSD2 polypeptide.

The specificity of the anti-peptide antibody was further evaluated by probing western blots of various sub-cellular fractions of kidney and placenta (FIG. 6).

A single band was detected in microsomes (lanes 1 and 2), the 1500 g pellet (lanes 3 and 4) and total homogenates (lanes 5 and 6) of placenta and kidney, respectively, co-migrating with the cloned 11 βHSD2 protein (lane 7). A lightly staining band of approximate molecular weight 40,000 daltons was sometimes detected in the pellet fractions and is most probably the result of degradation during fractionation and extraction, as this species was not observed in lanes containing the total homogenates.

EXAMPLE 10

A Diagnostic Assay for Predicting the Success of IVF Embryo Transfer Procedures

High levels of 11 βHSD enzyme activity in the ovary may be inhibitory to successful embryo transfer and implantation following IVF (Michael et al., 1993). Measurement of ovarian 11 βHSD2 gene expression indicates whether a female patient is a suitable candidate for IVF and embryo transfer procedures.

Granulosa cells are isolated from follicles collected from female patients, and cultured as described by Michael et al. (1993). Cell extracts are prepared as described in earlier Examples. Levels of 11 βHSD2 protein in cell extracts is measured by ELISA, or other immunological assay using known quantities of the synthetic peptide PEP-3 set forth in SEQ ID NO: 3, as a standard reference. The primary antibody is anti-peptide IgG referred to in Example 8, which is specific for the 11 βHSD2 enzyme. The second antibody is a horseradish peroxidase-conjugated goat anti-(rabbit IgG) serum. Reactions are carried out in microtitre wells and read in a microtitre plate reader.

EXAMPLE 11

A Diagnostic Assay for Determining the Hypertensive Condition of a Patient

Low levels of 11 βHSD2 enzyme activity, resulting in high cortisol:cortisone ratio in the kidney is a prognostic indicator of hypertension. Biopsies of skin tissue, or renal cells are collected and extracts prepared as described in the foregoing examples. The 11 βHSD2 protein content of these extracts is determined by ELISA, or other immunological assay technique, as described in Example 10.

EXAMPLE 12

An Assay for Identifying Modulators of glucocorticoid Metabolism

Chemical compounds that modulate 11 βHSD2 activity are screened using the expression assay described in the foregoing Example 5 to Example 7 inclusive. Briefly, CHOP cells transfected with pHSD2 are incubated for 60 hours at 37° C. Cellular homogenates are prepared and assayed in the presence of 2 nM [$^3$H] cortisol, 10 nM cortisol and varying concentrations of a chemical compound being tested for agonist or antagonist activity. Alternately, the cellular homogenate is fractionated to isolate the 11 βHSD2 polypeptide in a more pure form, using procedures well known to one normally skilled in the art, including ion-exchange chromatography, gel-filtration, hydrophobic interaction chromatography, or a combination of these procedures, amongst others. Kinetic constants characterising the affinity of 11 βHSD2 for agonists and antagonists are evaluated further, from measurements of initial velocities of reactions, as described in Example 6.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. Agarwal, A. K, Monder, C., Eckstein, B. and White, P. C (1989) J. Biol. Chem. 264, 18939–18946.
2. Agarwal A K, Mune T, Monder C, White P C, NAD-dependent isofom of 11beta-hydroxysteroid dehydrogenase. 1994 J. Biol. Chem. 269:25959–25962.
3. Alliet, P., Lu, R. B., Madraxo, D. L. G. J., Santer, R., Lebenthal, E. and Lee, P. C. (1989) J. Steroid Biochem. 33, 1097–1102.
4. Arriza, J. L., Simerly, R. B., Swanson, L. W. and Evans, R. M. (1988) Neuron 1, 887–900.
5. Ausubel, F. M., Brent, R., Kingston, R. E., Moore, D. D., Seidman, J. G., Smith, J. A., and Struhl, K. (1987). Current Protocols in Molecular Biology. Wiley Interscience (ISBN 047150338)
6. Beaumont, K. and Fanestil, D. D. (1983) Endocrinology 113, 2043–2049.
7. Berndt M C, Gregory C, Kabral A, Zola H, Fournier D, Castaldi P A, Purification and preliminary characterization of the glycoprotein Ib complex in the human platelet membrane. 1985 Eur J Biochem. 151: 637–649
8. Berndt M C, Chong B H, Bull H A, Zola H, Castaldi P A, Molecular characterization of quinine/puinidine drug-dependent antibody platelet interaction using monoclonal antibodies. 1985 Blood. 66: 1292–1301
9. Brown R W, Chapman K E, Edwards C, Seckl J R Human Placental 11-beta-Hydroxysteroid Dehydrogenase—Evidence for and Partial Purification of a Distinct NAD-Dependent Isoform 1993 Endocrinology. 132:2614–2621.
10. Douillard and Hoffman (1981). Basic Facts about Hybridomas. In: Compendium of Immunology Vol II (ed. Schwarz)
11. Edwards C R, Stewartt P M, Burt D, Brett L, McIntyre M A, Sutanto W S, deKloet E R, Monder C Localisation of 11 β-hydroxysteroid dehydrogenase-tissue specific protector of the mineralocorticoid receptor 1988 Lancet. 2:986–9
12. Edwards, C., Benediktsson, R., Lindsay, R. S. and Seckl, J. R. (1993) Lancet 341, 355–357
13. Funder, J. W., Pearce, P. T., Smith, R. and Smith, A. I. (1988) Science 242, 583,585
14. Funder, J. W., Pearce, P. T., Myles, K. and Roy, L. P. (1990) FASEB J. 4, 3234–3238
15. Haseloff, J., and Gerlach, W. L., (1988) Nature 334:586–594
16. Heffernan, M., and Dennis, J. W. (1991) Nucleic Acids Res. 19, 85–92
17. Kohler and Milstein (1975) Nature, 256:495–499
18. Kohler and Milstein (1976) Eur. J. Immmunology, 6:511–519
19. Krozowski, Z. S. and Funder, J. W. (1983) Proc. Natl. Acad. Sci. USA 80, 6056–6060
20. Krozowski, Z., Stuchbery, S., White, P., Monder, C. and funder, J. W. (1990) Endocrinology 127, 3009–3013

21. Lerner R A, Green N, Alexander H, Liu F T, Sutcliffe J G, shinnick T M, Chemically syntheized peptides predicted from the nucleotide sequence of the hepatitis B virus genome elicit antibodies reactive with the native envelope protein of Dane particles. 1981 Proc Nati Acad Sci. 78:3403–3407
22. Mercer W R, Krozowski Z S Localization of an 11 betta hydroxysteroid dehydrogenase activity to the distal nephron. Evidence for the existence of two species of dehydrogenase of the rat kidney. 1992 Endocrinology. 130:540–3
23. Michael, A. E., Gregory, L., Walker, S. M., Antoniw, J. W., Shaw, R. W., Edwards, C. and Cookke, B. A. (1993) Lancet 342, 711–712
24. Monder, C. (1991) J. Steroid Biochem. Mol. Biol. 40, 533–536
25. Monder, C., Hardy, M. P., Blanchard, R. J. and Blanchard, D. C. (1994) Steroids 59, 69–73
26. Naray-Fejes-Toth A, Frejes-Toth G Glucocorticoid receptors mediate mineralocorticoid-like effects in cultured collecting duct cells 1990 Am J Physiol. 259 F672–F678
27. Naray-Fejes-Toth A, Watlington C O, Fejes-Toth G 11 beta-Hydroxysteroid dehydrogenase activity in the renal target cells of aldosterone 1991 Endocrinology. 129:17–21
28. Naray-Fejes-Toth, A., Rusvai, E., Denault, D. L., Stegermain, D. L. and Fejes-Toth, G. (1993) Am. J. Physiol. 265, F896–F900.
29. Nikkila, H., Tannin, G. M., New, M. I., Taylor, N. F., Kalocitzoglou, G., Monder, C., and White, P. C. (1993) J. Clin. Endocrinol Metab. 77, 687–691.
30. Rusvai E, Naray-Fejes-Toth A A New Isoform of 11-beta-Hydroxysteroid Dehydrogenase in Aldosterone Target Cells 1993 J Biol Chem. 268: 10717–10720
31. Sasano H, Fukushima K, Sasaki I, Matsuno S, Nagura H, Krozowski Z S, Immunolocalization of Mineralocorticoid Receptor in Human Kidney, Pancreas, Salivary, Mammary and Sweat Glands—A Light Electron Microscopic Immunohistochemical Study 1992 J Endocrinol. 132:305–310
32. Steward, P. M., Murry, B. A. and Mason, I. J. (1994) J. Clin. Endocrinol. Metab. 79, in press
33. Ulick S, Levine S L, Gunczler P, Zanconato G, Ramirez L C, Rauh W, Rosler A, Bradlow L H, New M I A syndrome of apparent mineralocorticoid excess associated with defects in the peripheral metabolism of cortisol. 1979 J Clin Endocrinol Metab. 49: 757–763
34. Wu, L., Einstein, M., Geissler, W. M., Chan, H. K., Elliston, K. O. and Anderson, S. (1993) J. Biol. Chem. 268, 12964–12969.

We claim:

1. An isolated nucleic acid molecule encoding a human NAD+ dependent 11 β-hydroxysteroid dehydrogenase.

2. An isolated nucleic acid molecule encoding a human NAD+ dependent 11 β-hydroxysteroid dehydrocenase having the amino acid sequence as set forth in SEQ ID NO: 2.

3. The isolated nucleic acid of claim 2, wherein the isolated nucleic acid is cDNA.

4. The isolated nucleic acid of claim 2, wherein the isolated nucleic acid is genomic DNA.

5. The isolated nucleic acid of claim 2, wherein the isolated nucleic acid is RNA.

6. A genetic construct comprising the nucleic acid molecule according to claim 2 operably linked to a promoter.

7. A genetic construct according to claim 2 capable of expression in a prokaryotic cell.

8. A genetic construct according to claim 2 capable of expression in a eukaryotic cell.

* * * * *